United States Patent [19]

Farrell

[11] Patent Number: 5,225,342
[45] Date of Patent: Jul. 6, 1993

[54] SYSTEMIC PLANT INTERFACE

[76] Inventor: Michael E. Farrell, 4707-4 Via La Paloma, Orange, Calif. 92669

[21] Appl. No.: 383,238

[22] Filed: Jul. 19, 1989

Related U.S. Application Data

[63] Continuation of Ser. No. 50,262, May 14, 1987, abandoned, which is a continuation-in-part of Ser. No. 916,600, Oct. 8, 1986, abandoned, which is a continuation-in-part of Ser. No. 869,160, May 30, 1986, abandoned.

[51] Int. Cl.⁵ .............. C12N 5/00; A01G 31/00; A01G 25/00; A01G 5/00
[52] U.S. Cl. .................. 435/240.45; 47/60; 47/62; 47/63; 47/64; 47/81; 47/41.12; 47/41.13
[58] Field of Search ............... 47/59, 60, 62, 63, 64, 47/65, 80, 81, 41.12, 41.13; 435/240.4, 240.45; 800/200

[56] References Cited

U.S. PATENT DOCUMENTS

| | | | |
|---|---|---|---|
| 3,842,539 | 10/1974 | Sacalis | 47/58 |
| 4,103,457 | 8/1978 | Carlisle | 47/58 |
| 4,403,446 | 9/1983 | Wolfe et al. | 47/58 |
| 4,531,324 | 7/1985 | Yang et al. | 47/81 |
| 4,586,288 | 5/1986 | Walton | 47/73 |
| 4,651,468 | 3/1987 | Martinez et al. | 47/80 |

FOREIGN PATENT DOCUMENTS

| | | |
|---|---|---|
| 0117766 | 7/1984 | European Pat. Off. . |
| 0167638 | 1/1986 | European Pat. Off. . |
| 8604919 | 8/1986 | PCT Int'l Appl. . |

OTHER PUBLICATIONS

Conger, B. 1981, p. 178 Dr: Cloning agricultural plants via in vitro techniques, Conger, B., ed., CRC Press, Inc.: Boca Raton, Fla.

*Primary Examiner*—David T. Fox
*Attorney, Agent, or Firm*—Adam Cochran

[57] ABSTRACT

A systemic plant interface replaces the roots of a growing plant by providing a perforate surface which mates to growing xylem tissue of a vascular plant and provides fluid communication and support necessary to sustain the aerial portions of a viable plant.

8 Claims, 10 Drawing Sheets

HAPLOSTELE  ACTINOSTELE  PLECTOSTELE  ECTOPHLOIC SIPHONOSTELE

AMPHIPHLOIC SIPHONOSTELE  DICTYOSTELE  EUSTELE  ATACTOSTELE

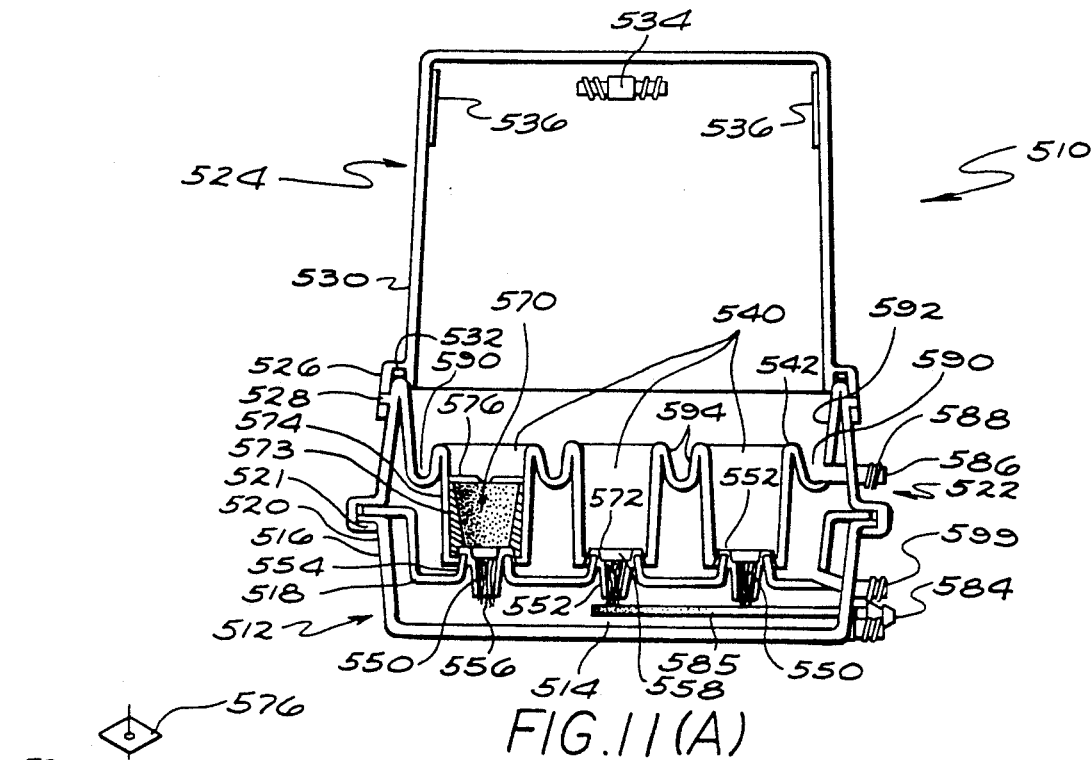
FIG.11(A)
FIG.11(C)
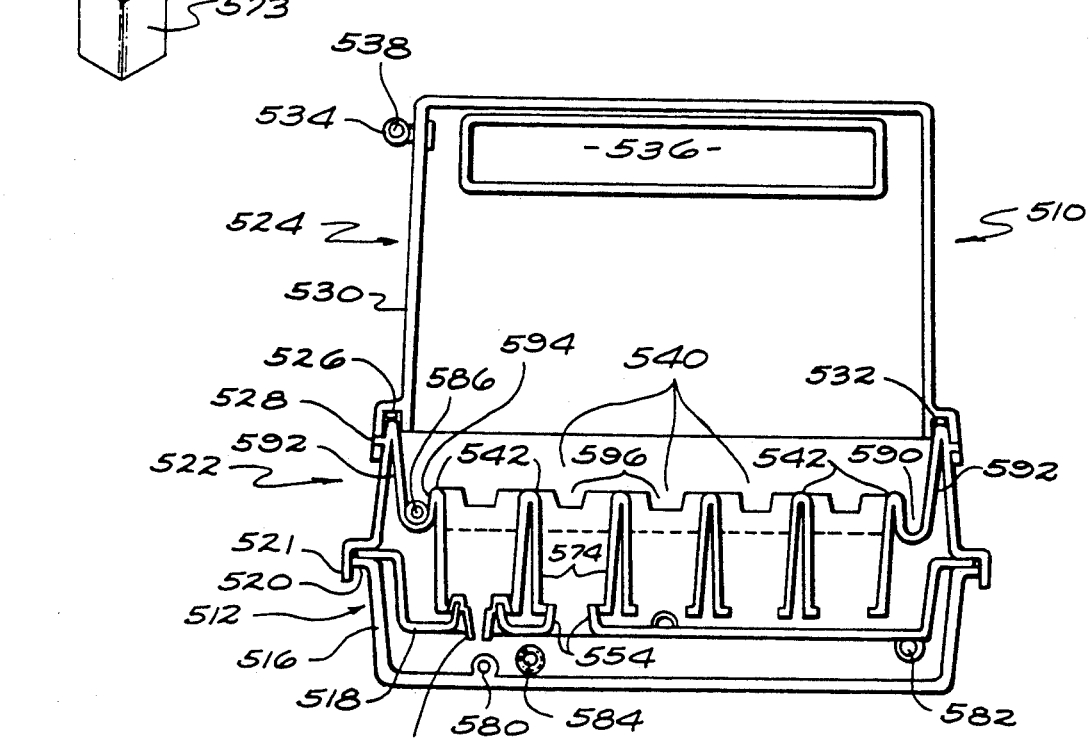
FIG.11(B)

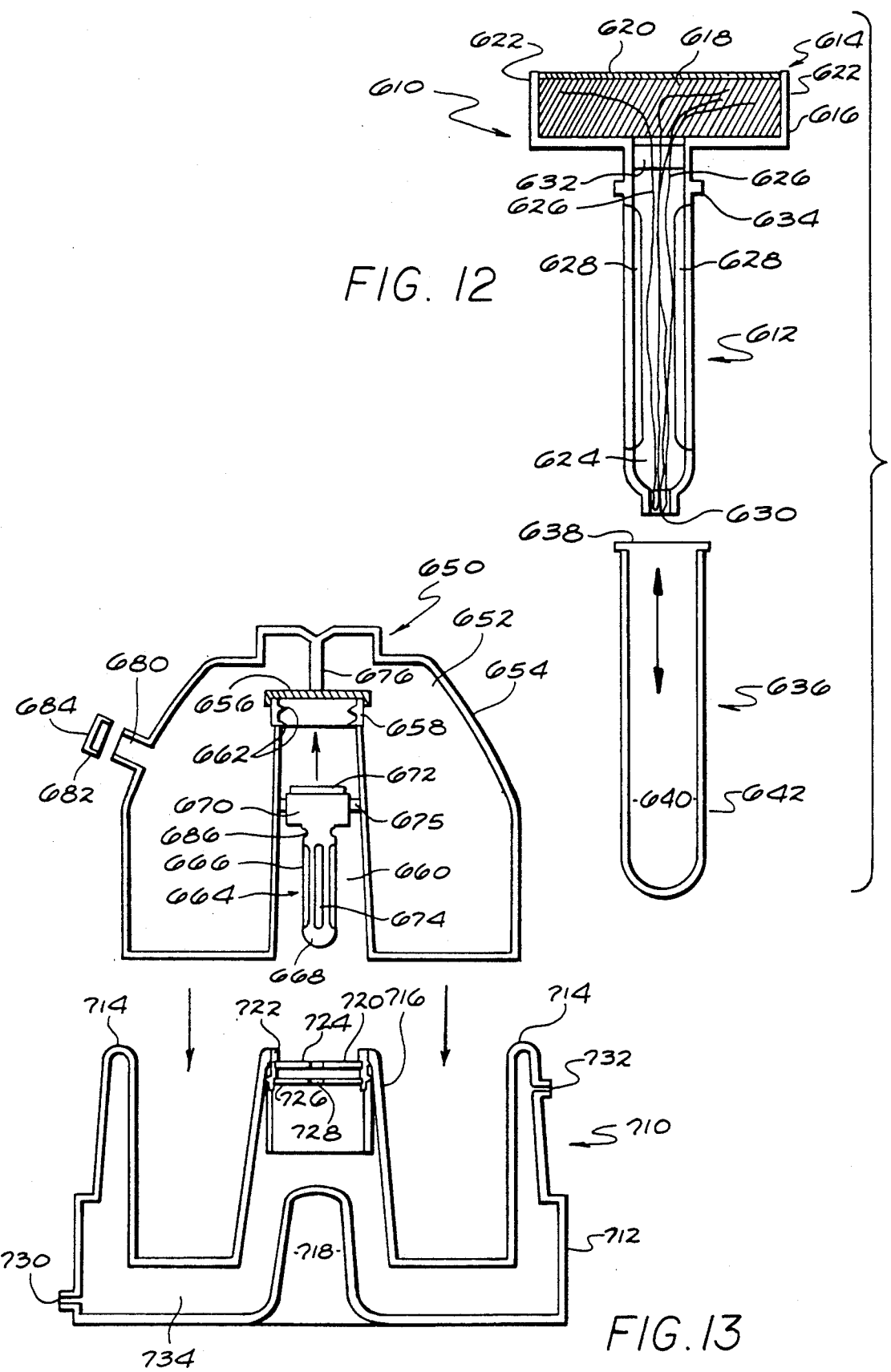

SYSTEMIC PLANT INTERFACE

This is a continuation of co-pending application Ser. No. 07/50,262 filed on May 14, 1987. now abandoned, which is a continuation-in-part of application Ser. No. 06/916,600, filed Oct. 8, 1986, now abandoned, which is a continuation-in-part of application Ser. No. 06/869,160, filed May 30, 1986, now abandoned.

FIELD OF THE INVENTION

This invention relates generally to the field of the botanical sciences, and more particularly to a systemic plant graft interface and support system.

BACKGROUND OF THE INVENTION

A plant is broadly defined as any member of the group of living organisms which, although characterized by irritability or excitability, is typically lacking in locomotor movement or rapid motor response. Plants may be divided into two classes: vascular and non-vascular plants. Non-vascular plants, e.g., bryophytes and algae, do not have vascular tissue which enables the circulation of nutrients and sap within the organism. This class of plants is not within the subject matter of this invention, and will not be discussed further herein.

Vascular plants are plants which have evolved physiologically complex conducting systems, and the efficiency of these vascular systems has led to tremendous ecological diversification. These plants range from grasses to large trees, and provide vegetables, fruit, flowers, wood and various photosynthates as products of plant growth and reproduction.

Vascular tissue is comprised principally of xylem and phloem. Xylem is the principal water and mineral-conducting tissue in vascular plants, and is a complex tissue composed of non-living, lignified tracheids, vessels and fibers and their associated living parenchyma cells. Xylem also may provide mechanical support, especially in plants with secondary xylem, i.e., wood. Xylem, while thus providing some mechanical support, functions primarily to convey water from the roots to the aerial portions of the plant.

Phloem tissue is that part of the vascular system which transports the elaborated food materials (photosynthates) from the leaves. The phloem consists typically of sieve tubes and companion cells. Transportation of the phloem is typically from leaves to roots.

Xylem tissue forms vascular paths along the long axis of the plant stems from roots to the tips of the aerial, i.e., above-ground, portions of the plant. From these longitudinal pathways extend radial xylem tissue, termed xylem rays, which conduct water and water nutrient solutions to the leaves, shoots and other surface portions of the plant. The phloem tissue forms a distinct pathway which surrounds the xylem.

The stems, that is, the above-ground portions of vascular plants, vary from plants less than 1.2 cm in height to forest giants towering 100 meters or more. Nonetheless, all stems have essentially similar vascular systems. The growing tip of any young stem has cells which are initially very similar, but which differentiate to form the plant subsystems as the stem grows. In most dicotyledonous plants, the cells which are nearest the center of the stem become xylem cells and those towards the circumference of the stem become phloem cells. In most monocotyledons, the vascular tissues occur in the form of separate small bundles with the phloem surrounding the xylem tissue.

Generally, fruit-bearing and other vascular plants are grown by placing a seed, sprout or other natural plant portion in fertile soil or hydroponic medium and allowing roots to form and extend to provide anchorage, and absorption of water and minerals which are conducted by the vascular system to the aerial portions of the plant which, in turn, provide the desired plant products.

It will be appreciated that traditional techniques for the propagation of plants consume substantial amounts of time and acreage. Many plants propagated by man for the production of fiber, wood, photosynthates, blossoms or fruits require long maturation cycles to afford requisite physical and nutritive support (i.e., roots) for the shoots which are the desired plant product.

Current techniques focus excessive resources toward optimizing growth for the entire plant when, in fact, the shoots' metabolic maximization is often the ultimate objective. Parenthetically, the term shoot is used herein to indicate any aerial stem of a vascular plant rather than the commonly-employed reference to a young growing branch or twig with leaves.

Attempts have been made to propagate plants in an artificial environment through the use of hydroponic techniques. In this soil-free culture method plants are grown with their roots immersed in a solution containing the necessary mineral salts, or rooted in a sand or vermiculite medium moistened with such a solution. This method, while providing certain advantages, is not totally efficient due to the necessity to support the entire plant when only minimal anchorage is supplied by the roots, and the fact that the nutrient solutions must be drained periodically to avoid oxygen starvation or dilute exuded toxins. Also, to the extent the growth solutions in hydroponic systems come in contact with ambient air and the bacteria therein, contamination of the growth solutions is an ongoing problem. Further, hydroponic methods have inherent difficulties because plants which have evolved to be rooted in a nutrient soil are required to root in an unnatural medium. For these reasons, most plants which are hydroponically grown are of the smaller, rapidly-maturing variety and large-scale hydroponic production of fruits and vegetables has not been economically feasible.

Workers in the plant sciences have developed techniques for forming plants from individual cells or tissues by placing shoot explants on a solid or liquid media in culture vessels. However, these techniques are applied to the regeneration of whole plants, that is, the propagation of plant cells or tissue to form roots and precursors of the aerial plant portions (i.e., roots and shoots) which are then further grown to form complete plants in either natural soil or under hydroponic conditions. During the early development of cultured plants, a high ambient humidity is required to protect the growing shoot, and as the shoot matures a gradual decrease to normal ambient humidity is required to progressively harden the plant prior to exposing the plant to natural growth conditions. Accordingly, it has been the practice to sequentially transfer the tissue culture, or to sequentially modify the humidity in a closed greenhouse to meet the requirements of the growing plant. Thus, the existing practice in applied botanical-horticultural science is to propagate and harden a whole plantlet or sapling, which is then deposited at a location where further maturation of the whole plant takes place. Accordingly, extended maturation periods, inflexible crop rotation, restrictive growing zones and requisite soil conditions significantly limit crop production.

Further, such micropropagation has posed unique problems for many tissues such as woody fruits, tropicals and ornamental plants due to the need to modulate or change nutrients over time. Multiple transfers of propagating tissues from one growth medium to another as the plant matures have thus been required to prepare the plant for growth in a natural environment.

While the in vitro propagation of plants has provided advantages, especially in the regeneration of plants from protoplast cells, many potential advantages of culture propagation have not been realized in practice due to the difficulty of culturing plant cells or tissues to mature plants. In fact, many species are resistant to micropropagation techniques. While I do not wish to be bound to any particular theory, this failure may be due to the fact that the growth media comprise an artificial interface for plant growth which fails to adequately support the developing plant.

SUMMARY OF THE INVENTION

The present invention furnishes a solution to many of the problems noted above with respect to the propagation and growth of whole plants and affords advantages not previously envisioned by workers in the plant sciences by providing an artificial replacement for the vascular and support functions normally provided by the root system of a plant. The invention includes a method for the growth of a vascular plant shoot by providing a synthetic, biocompatible interface for the direct exchange of nutrient fluid with the shoot's living vascular tissue, thus forming a plant which comprises an aerial portion which grows and produces plant products in the absence of roots. The synthetic vascular interface may be adapted to support the branch or other shoot growing therefrom to permit the manipulation of plant tissue at a systemic level.

Substantial advantages are provided by the invention. For example, in whole plants the development period from the juvenile state to the mature crop-producing state may be as long as three to seven years. For example, fruit trees do not produce fruit, i.e., ripened ovaries, until a nearly mature root and trunk system is produced, and substantial fruit yields from such trees do not occur until the trunks and branches are of sufficient thickness and metabolic maturity to support the fruit. Since the apparatus and method of the present invention allow the growth of branches without the need for roots or any main stem (trunk), the period of time for the growth and maturation of roots and trunks is unnecessary and only the time for the growth of the product-bearing branches, potentially a single season, is required. Further, since a large portion of the total area of a tree is devoted to non-fruit-producing portions, and wide spacing of producing trees is required to avoid interference between the respective root systems, substantial space savings are achieved.

Due to the direct systemic vascular interface, nutrient solutions may be employed which maximize the production of flowers, fruits or other products. In contrast to naturally growing shoots, where the supporting tissues other than the producing shoots extract a tariff for the supporting functions, the nutrient solutions flow directly from the synthetic interface to the producing branches.

The systemic interface of the invention includes an artificial and biocompatible xylem means, preferably a perforate surface such as that formed by a cross-section of a plurality of parallel hollow fibers, and means for applying a flow of nutrient solution to the xylem means such as by applying a flow of such solution to the perforate surface. The apparatus further includes absorption means which form an artificial and biocompatible phloem system.

The apparatus is employed in a method for growing a plant o r plant portion, which includes placing a totipotent plant cell, that is, a cell capable of growing and developing into an entire organism (preferably in the form of a shoot explant), on the artificial xylem surface and applying nutrient solutions in a manner which encourages the growth of the cell or explant to form aerial portions of the plant and which essentially prohibits the growth of plant roots.

Accordingly, a growing rootless vascular plant is formed which comprises a shoot having a periderm and containing xylem and phloem tissue within the vascular system of the shoot, the shoot growing from a systemic interface including an artificial xylem means mated to and permitting fluid communication with the xylem tissue of the shoot, and an artificial phloem means mated to and permitting fluid communication with the phloem of the shoot. Further, the plant includes retaining means abutting the periderm of the shoot and adapted to support the shoot on the systemic interface and maintain the fluid communication of the interface with the xylem and phloem tissue, and means for providing a nutrient solution to the shoot. The vascular plant thus described grows in the absence of roots.

In another aspect of the invention, the systemic interface is used to form a culture carousel for the in vitro growth of cells on tissue to form shoots, and provides a means for the support of the growing shoots in a manner which offers substantial advantages over existing agar techniques. Means are also provided for the modification of the humidity within the culture vessel while maintaining sterility by the sequential removal of relatively impermeable portions of the vessel.

BRIEF DESCRIPTION OF THE DRAWINGS

FIG. 11(A) is a schematic cross-sectional end view of a plant growth chamber useful in forming roots on established shoots in communication with the artificial plant interface, so that transplanting to a natural environment is facilitated;

FIGS. 11(B) and 11(C) are a schematic cross-sectional side view of the chamber shown in FIG. 11(A);

FIG. 12 is a cross-sectional side view of a transferrable xylem interface which facilitates transfer of an established shoot to hardening environments; and FIG. 13 is a schematic cross-sectional view of a plant growth cartridge, for example, a rooting cartridge, which employs the xylem interface shown in FIG. 12.

DETAILED DESCRIPTION OF A PREFERRED EMBODIMENT

Figure 1:
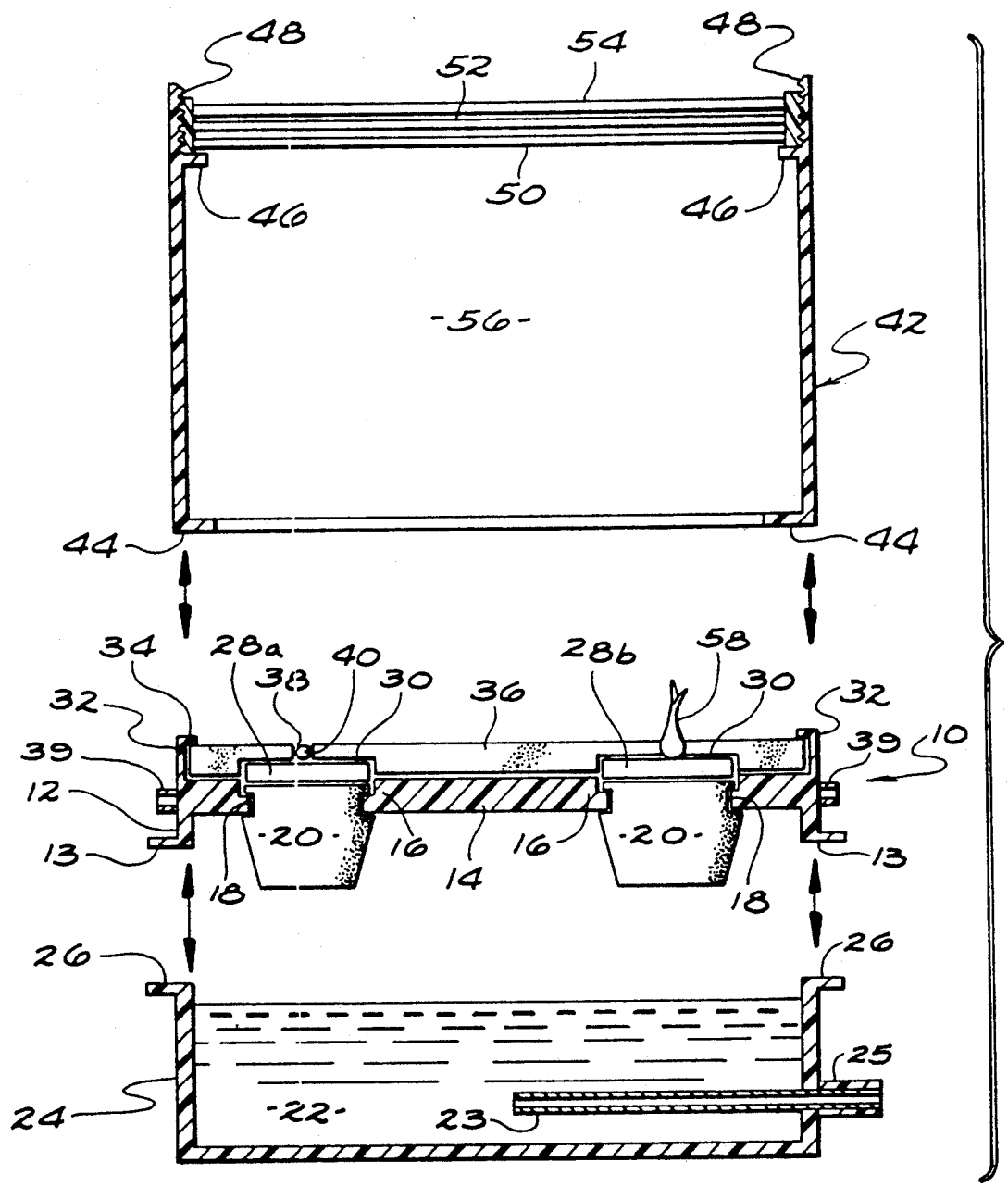
FIG. 1 is an exploded side elevational view in cross-section, of an in vitro tissue culture carousel according to the present invention.

In the embodiment hereinafter set forth, the present invention will be described with respect to the growth of branches of *Ficus carica* and various other fruit-producing vascular plant species with the artificial systemic interface of the invention. However, it is to be understood that this embodiment merely exemplifies the invention, which may be applied to any growth of any vascular plant in the absence of roots. Therefore, specific functional details are not necessarily to be interpreted as limiting, but rather as a basis for the claims.

The invention proceeds by providing a factitious interface which serves the support and nutrient functions of natural plant roots. The words factitious or artificial, as used herein, are meant to convey the meaning of being made by art or science, in distinction from what is produced by nature. Factitious xylem and phloem interfaces are provided which allow growth of callus tissue which is fed with selected hormones to prohibit root formation and encourage the growth of the desired aerial plant portions.

As set forth above, when callus cells grow under the influence of appropriate plant hormones, they gradually change in form. Those cells which are nearest the center of the stem differentiate into xylem cells, the water- and mineral-conducting tissues, and those toward the circumference mature as phloem cells, the principal food-conducting tissue of the plant. The vascular system and its associated ground tissue is commonly referred to as the stele of the plant. Various types of stele exist, each plant exhibiting a particular type. However, each stele type includes one or more internal xylem channel surrounded by phloem tissue.

The artificial xylem interface includes a biocompatible surface having perforations of a size and shape which approximate the xylem lumens in the target plant's vascular system. Preferably, the xylem interface is formed from a plurality of parallel hollow fibers which are bundled longitudinally to present a porous surface and permit nutrient solution to pass through the lumens of the hollow fibers. Hollow fibers which have been found to be effective are those sold by the Celanese Company of Charlotte, N.C. under the trademark Cel-Guard M.H.F. and by Mitsubishi Rayon Division of Tokyo under the trademark K.P.F.-200.

For example, xylem interface for the growth of a ficus branch may be constructed of hollow polypropylene fibers having a lumen diameter of from 30 to 65 microns. Both ends of the hollow fiber are sealed with a biocompatible material such as urethane so that the nutrient solution passes only through the lumens of the hollow fibers rather than between the fibers. A urethane sold under the trademark Medithane 3905 by the Hexcel Corporation has been found to be effective for this purpose. Preferably, the wall fibers are constructed to have a porosity which is sufficient to allow oxygenation of the nutrient solution by passage of air or oxygen around the outside of the fibers under a positive pressure (referred to herein as membrane oxygenation). Alternatively, oxygen may be sparged through the solution to permit bubble oxygenation of the nutrient fluid.

When appropriate callus or shoot tissue is seated on the xylem interface, and supplied with the appropriate nutrient solution, cell growth occurs both radially and longitudinally from the xylem interface in a manner which is identical to the growth of shoot, stem or branch tissue in a natural tree. As the tissue expands radially, natural xylem tissue is formed which mates with the perforate surface of the xylem interface, and this developing xylem tissue is surrounded by natural phloem in the developing shoot.

In order to complete the vascular system within the artificial systemic interface, an artificial phloem means is provided which mates and permits fluid communication with the developing phloem tissue of the shoot. Preferably, the artificial phloem means comprises a porous sieve material which will mate with the developing phloem tissue and allow the removal of sap from the developing shoot. Preferably, a biocompatible open-cell sponge is disposed around the callus tissue and functions as a phloem interface by permitting the return of excess feeding solution and phloem vascular sap. As the limb develops from callus tissue, the phloem tissue grows into the open-cell material. Since the phloem interface means is biocompatible (i.e., will sustain the growth of living plant tissue) it becomes unitary with the natural phloem tissue in the sense that it allows the natural phloem cells to interface with the artificial phloem means so that phloem juices flow from natural phloem tissue to the interface. The artificial phloem is porous to the extent that phloem juices may be conducted away from the natural phloem tissue.

An open cell sponge-like neointimal material which mates with and drains fluid from the natural phloem is preferred for the artificial phloem, and a polyvinyl acetyl or dacron-velour sponge sold by Americal Corporation under the trademark Merocel has been found to be particularly advantageous. This material is biocompatible and the plant tissue grows naturally into the open cells. In this regard, it is to be understood that the word neointimal as used herein is used to convey the meaning of an artificial material into which living tissue will grow naturally. Thus, a neointimal sponge is preferred as the phloem interface.

Any cell or explant capable of growing and developing into an entire plant organism, that is, any totipotent plant isolate, may be employed with the systemic plant interface. Many isolated cells of a mature plant are totipotent, but those which lack cytoplasm and nucleus are not. For example, mature tracheids, fibers and sclereids are not totipotent cells. Protoplasts are specifically included within the definition of totipotent plant isolates. In the growth of fruit tree limbs, isolates from the apical meristem tissue are preferred. The meristem is a localized tissue in which rapid mitotic cell divisions occur. The apical meristem is that group of meristemic cells at the tip of a shoot from which all the tissues of the mature plant axis originate.

When totipotent plant tissue is cultivated in an artificial culture medium, unorganized cell multiplication may occur to form a wound-like tissue referred to as callus, or adventitious shoots may form directly from the explant. Since a totipotent explant contains the genetic instructions necessary for the development of a whole plant, the proliferation induced by the present invention must be directed toward the formation of the aerial plant portions rather than roots. For this reason it is preferred that the enclosure or other apparatus surrounding the growing plant isolate be translucent or transparent, since actinic (plant growth stimulating) radiation may have an inhibitory effect on root growth.

As is known in the art, growth or nutrient media or various growth solutions may be employed to stimulate or inhibit certain directions of cell, tissue and organ growth. As used herein, such growth media or growth solutions include mineral salts and vitamins necessary for plant growth, generally containing combined nitrogen, potassium, phosphorous, calcium, sulphur and magnesium with traces of iron, boron, zinc, copper and various organic substances which stimulate the growth of shoots, branches or other desired aerial plant portions while inhibiting root growth. The growth media employed in the various steps hereinafter described may be any medium understood by those skilled in the art to provide hormones and nutrients necessary for such growth. As used herein, the term hormone refers to an organic compound, either natural or synthetic, that modifies or controls one or more specific morphological, physiological or biochemical processes within the plant.

While the exposure of the callus cells to actinic radiation is a substantial root-inhibiting factor in some instances, the use of certain root-stimulating hormones and nutrients known to induce root formation should be avoided. For example, while auxins promote growth along a longitudinal axis in plants, and are known to induce flowering in some species, one of the principal uses of synthetic auxins has been to promote the formation of roots on stem cuttings and accordingly the use of auxins at concentrations which stimulate root growth in the nutrient solutions should be avoided. Further, root-forming hormones such as indolebutyric acid and 3-aminopyridine should also be avoided. Generally, an auxin-to-cytokinin ratio of less than 1-to-1 (on a molar basis) is advantageous in promoting the formation of shoots over roots. Zeatin riboside and gibberellic acid are also known to induce shoot formation over root production. Of course, the need for means to inhibit the formation of roots as the plant isolate matures may vary depending on the particular species. Accordingly, the preferred transparent or translucent housing for the artificial plant interface may not be necessary in all instances. For example, root formation in many woody species does not occur spontaneously even under appropriate culture conditions.

Due to the nature of the growth solutions (tissue culture media) which facilitate the development of contaminating organisms, it is necessary to maintain the tissues, media containers and associated apparatus under sterile conditions to avoid growth of bacteria, virus and fungi which would otherwise overwhelm the plants. Accordingly, the appropriate cells or tissues are isolated under clean room conditions. With respect to cells, the apical meristem of selected limbs of targeted species is isolated and introduced into a sterile solution of cellulase and glucose. The enzyme induces the dissociation of the tissue into individual cells, which are isolated and inoculated into appropriate growth media to stimulate callus formation. As to explant tissue or callus from cell culture, the callus tissue is placed on a perforate surface having a plurality of apertures which are of an appropriate size and shape to mate to and permit fluid communication with the xylem tissue of the target plant, that is, the xylem tissue which will develop from the cell culture. Preferably, the xylem-mating perforate surface is comprised of the transverse cross-section of a plurality of lumenous fibers, the cross-section thus presenting a surface upon which the callus or other plant tissue can grow to form mating natural xylem tissue having vascular pathways which communicate directly with the lumens of the fibers. For this reason, the perforate surface, and thus the hollow fibers, should be biocompatible so that growth of and bonding to the xylem tissue is encouraged. To avoid the flow of growth solution between the hollow fibers rather than through the lumens, it is preferred that the fibers be bonded one to another by a biocompatible material. This material then provides an aseptic seal around each hollow fiber and functions as an interface substrate to the vascular system of the developing plant. However, in instances where a perfect biocompatible union between the fibers and natural xylem does not occur, symplastic transport between the tissue and the fibers will often be suitable for sustaining shoot growth.

The hollow fibers can be produced in various diameters, and with various lumen sizes or shapes depending upon the vascular system of the target plant. Generally, it has been found that a perforate surface which approximates the transverse cross-section of a haplostele provides superior results with most plants. A haplostele is a cylindrical protostele, i.e., a solid column of vascular tissue with the xylem centrally located and surrounded by phloem, having a smooth margin in transection.

Figure 8:
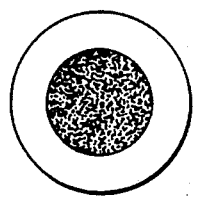
FIG. 8 is a schematic cross-sectional view of hollow fiber configurations.
Figure 8:
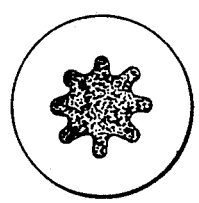
Figure 8:
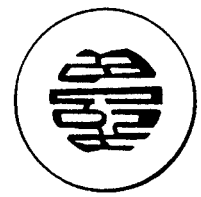
Figure 8:
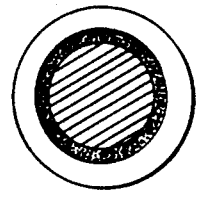
Figure 8:
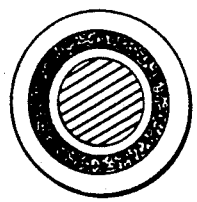
Figure 8:
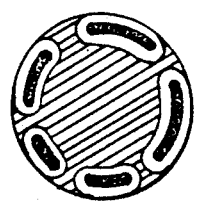
Figure 8:
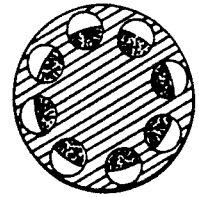
Figure 8:
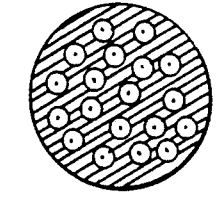

Other types of stele may be employed for a variety of plants, and transections of various types of stele are shown in FIG. 8 wherein the xylem tissue is shown as a darkened area, the phloem in white, and the central pith denoted by cross-hatching. For example, the actinostele is similar to the haplostele but the xylem passageway is arranged with radiating star-shaped rays. The plectostele is shown to be a protostele which further includes bands of phloem across the xylem passageway when viewed in cross-section.

Dictyostele and eustele are seen to comprise separate vascular bundles, each termed a meristele, and including both xylem and phloem. These vascular bundles are disposed around a central pith. The amphiphloic siphonostele is seen to have a central pith area and a xylem cylinder with phloem both interior and exterior to the xylem, as is the ectophloic siphonostele. The atactostele is seen to consist of vascular bundles scattered throughout the parenchyma tissue ©f the stem. This type of stele is characteristic of monocotyledons. In all of these steles, all or a substantial part of the vascular phloem is in fluid communication with the external phloem cells.

The outer cylindrical size of the hollow fiber membranes of the invention are of a size and diameter which comports with the dimensions of the xylem tissue of the mature plant. Generally, hollow fiber transections having a lumen diameter of less than 100 microns, preferably 30 to 65 microns, and an overall cylindrical diameter of 150 microns or less are preferred.

The hollow fibers can be made from a variety of biocompatible materials and by methods which are known in the art. Generally, the hollow fibers are made by forming the desired shape in a polymeric tube having a diameter of 1 or 2 cm or less and a length of about 1 meter, and then drawing or extruding this rod to the appropriate diametral dimension. Any desired porosity may be generated by chemical leaching, gamma radiation or other known means.

As stated above, the explant tissue is placed on the artificial xylem surface under sterile conditions. A nutrient solution is then presented to the callus tissue either by capillary action, i.e., by natural flow through the lumens, or if the fibers are of sufficient length to restrict such natural flow a low pressure solution feed, e.g., two pounds per square inch, may be applied to overcome the fluid friction in the lumens. As the tissue grows, the natural xylem tissue mates to the artificial xylem surface, and the natural phloem tissue begins to grow into the artificial phloem means as the callus expands radially, thus ensuring fluid communication between the natural phloem tissue and the porous phloem means of the graft interface. Natural capillary flow in the phloem sponge aids the natural translocation within the growing plant portion. If necessary, draining means may be associated with the phloem sponge to assist in the removal and/or recirculation of fluid from the plant Phloem. The hollow fibers have a porosity sufficient to provide for the automatic bleed-off of trapped air thus reducing the risk of "air-locking", which adversely affects the growth of plant tissue. This function mimics the action of natural plant tissue. Further, the porosity of the hollow fibers permits the membrane oxygenation of the nutrient solutions, as further described with respect to the drawings.

Turning now to the drawings, the invention will be described in more detail. FIG. 1 illustrates a tissue culture carousel 10, which includes legs 12 and a supporting member 14. The carousel 10 includes, in the member 14, a plurality of apertures 16 having annular flanges 18 as shown. Disposed in the apertures 16, and resting on the flanges 18, are capillary sponges 20 which extend sufficiently below the member 14 to contact a growth or nutrient solution 22 which is dispersed in a cup member 24 having flanges 26 which are adapted to mate and seal with the flanges 13 on the carousel 10 by means which are not specifically described by a particular reference numeral.

Resting directly above, and in abutting contact with the capillary sponge 20, there are seen discs 28a and 28b, respectively, on the left and right of the Figure. These discs will be described in more detail with respect to FIG. 5, but briefly comprise longitudinal hollow fibers disposed vertically with respect to FIG. 1. It will be apparent from the Figure that when the carousel 10 is lowered to mate with the cup member 24 as described, and the capillary sponges 20 are immersed in the solution 22, the solution will be drawn toward the discs 28 by capillary action, which will continue the flow of the growth solution 22 to the top surface 30 of the discs 28.

The carousel 10 is seen to further include upper arms 32, terminating in flanges 34, which laterally enclose a biocompatible, neointimal phloem sponge 36. Disposed in the sponge 36 and centered above the discs 28 are phloem sponge apertures, as shown by the reference numeral 38 above the disc 28a. It will be apparent from the drawing that the solution 22, having previously been described as flowing to the top surface 30 of the disc 28 by capillary action, will similarly be drawn into the sponge 36. Excess nutrient solution and fluids transported by the natural phloem tissue of the growing shoot may drain through the ports 39 in the carousel 10 into receiving means not specifically shown.

With respect to the disc 28a meristem, shoot tip or callus tissue 40 has been placed within the aperture 38, and directly upon the disc 28a. The tissue 40 has been formed from a totipotent plant isolate.

Following placement of the explant tissue 40 on the disc 28a, a cover 42, including a flange 44 at the lower edge thereof, may be lowered so that the flange 44 is brought into mating contact with the flange 34 of the carousel 10. The cover 42 may be fixedly attached to the carousel 10 by means which are not specifically shown. At an upper end of the cover 42, a flange 46 and annular threads 48 are seen to secure a series of transparent caps 50, 52 and 54 which maintain the humidity formed by evaporation of the nutrient solution 22 within a cavity 56 which is formed above the carousel 10. The cap 50 is non-permeable by moisture but as the callus 40 grows radially and longitudinally to form a shoot the cap 54 is removed and the partially permeable cap 52 and the permeable cap 54 left in place, so as to begin the adjustment of the developing shoot to ambient humidity. As shoot development continues, the cap 52 is removed and the more permeable cap 54 remains until the hardening process is completed. The developing plant can thus be adjusted to ambient humidity without disrupting the sterility of the cavity 56 or requiring transfer of the growing shoot from one container to another.

Turning now to the disc 28b in FIG. 1, a shoot 58 is shown to have developed over a period of about eight weeks from the initial explant tissue such as that designated by the reference numeral 40. The base portion of the shoot 58 which abuts the top surface 30 of the disc 28b has expanded radially and the shoot tissue has grown into the area of this phloem sponge 36 which surrounds the shoot 58. The fact that essentially all of the structural apparatus of the carousel 10, the cup 24 and the cover 42 are transparent, aids in growing of the shoot 58 in the absence of roots. The cup 24 includes a porous and hydrophobic oxygen sparging probe 23, which admits oxygen to the solution 22 through an external oxygen fitting 25 so that the oxygen content of the solution 22 can be maintained for optimal plant growth.

Figure 2:
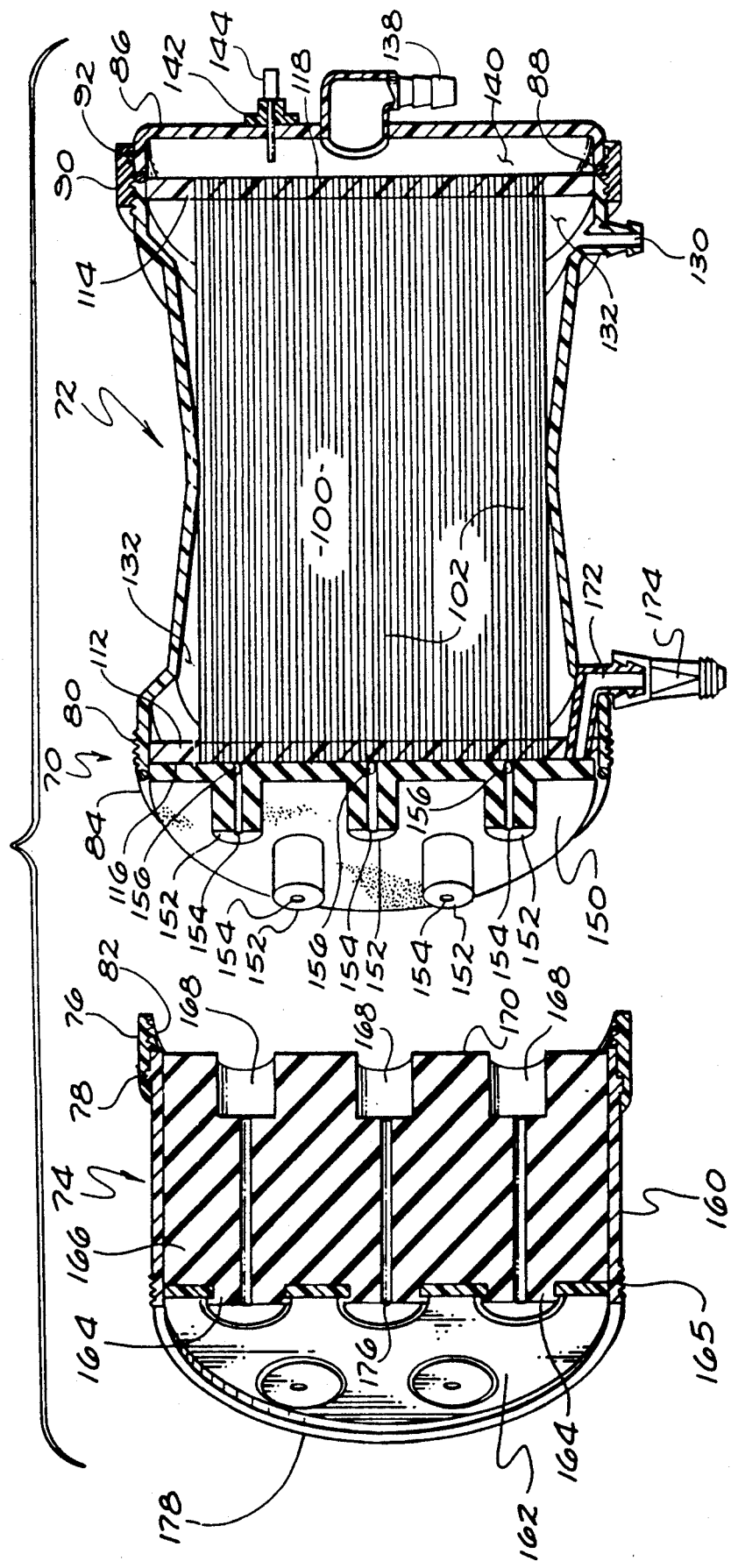
FIG. 2 is a partially exploded cross-sectional side elevational perspective view of a systemic plant interface for the growth of field plants in the absence of roots.

An artificial graft interface adapted for the growth of mature branches is shown in FIG. 2. In that Figure, a graft interface 70 is seen to include a first portion 72 and a second portion 74, which may be brought into mating engagement and secured by a bracket 76 which rotates about a flange and groove combination 78 and, through the engagement of external and internal threads 80 and 82, respectively, causes the first and second portions 72 and 74 to abut and seal at the O-ring 84.

At an opposite end of the first portion 72, an end cap 86 is releasably secured to the portion 72 by an O-ring 88 and a bracket 90 which bears on a flange and groove combination 92 and mating internal and external threads 94.

The outer casing of the interface 70 is preferably formed from transparent or translucent polymeric material, although minor parts such as the brackets 76 and 90 or other components nearer the end cap 86 may be opaque or darker if desired. However, the shoot-containing second portion 74 and the areas of the portion 72 immediately adjacent thereto may be transparent or translucent to assist in the inhibition of the formation of roots in the developing explant tissue.

Figure 3:
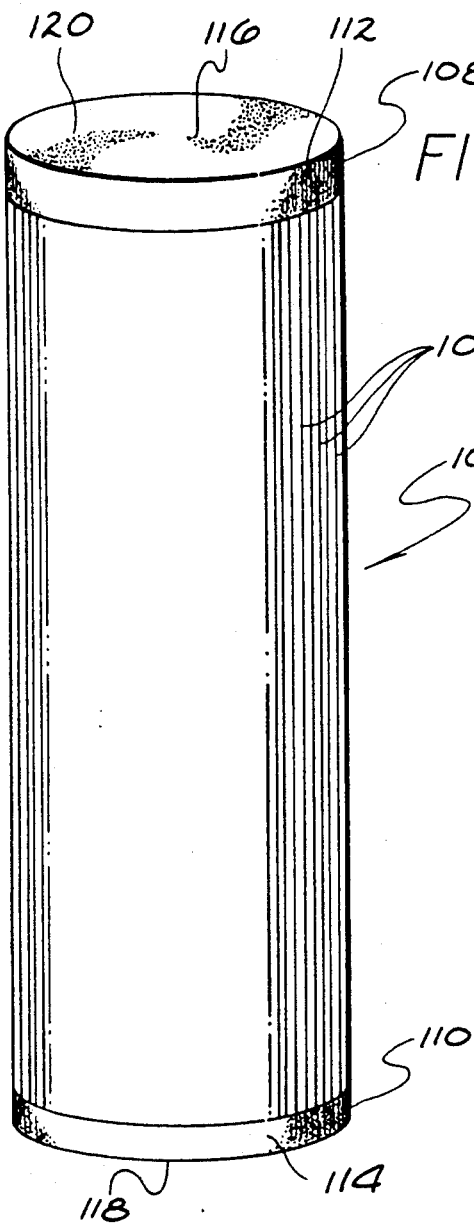
FIG. 3 is a perspective view of an artificial xylem interface employed in FIG. 2.

Disposed within the portion 72 is a hollow fiber assembly 100. In FIG. 3, the assembly 100 includes a plurality of hollow fibers 102 which are disposed longitudinally to the long axis of the assembly 100. As is shown in FIG. 4, each of the fibers has a shape similar to a haplostele in natural vascular plant tissue, that is, a hollow fiber 102 having a cylindrical wall 104 enclosing a lumen 106.

In FIG. 3, it should be noted that both ends 108 and 110 of the assembly 100 are sealed in cast sealing members 112 and 114, respectively, formed from biocompatible urethane or similar resin. After casting, the ends 108 and 110 are cut essentially perpendicular to the longitudinal axis of the assembly 100 to form perforate surfaces 116 and 118. With respect to the fiber discs 28 shown in FIG. 1, FIG. 5 shows a disc 28 which has been formed by sealing the plurality of fibers 102, such as are described with respect to FIG. 3, in the urethane casting material 120 throughout the length of the assembly 100, and thereafter, cutting the individual discs 28 from the assembly 100 in a manner which does not obscure the fiber lumens.

Figure 4:
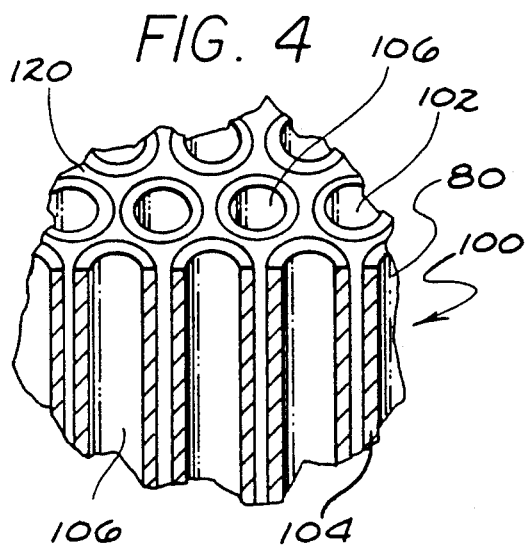
FIG. 4 is a perspective view of a portion of the artificial xylem interface described with respect to FIGS. 3 and 5.
Figure 5:
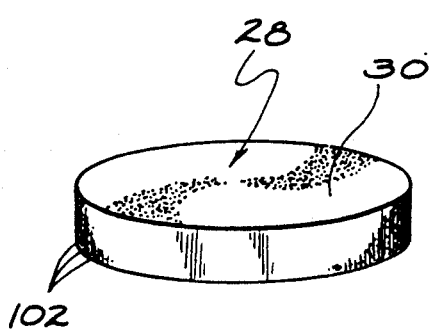
FIG. 5 is a perspective view of a xylem interface disc described in more detail in FIG. 1.

In FIG. 4, the perforate surface formed as described with respect to FIGS. 3 and 5 includes the urethane casting material 120 which fills the interstices between the hollow fibers 102, thus sealing the fibers and permitting fluid flow through the assembly 100 only through the lumens 106. In this embodiment, the fibers are disposed to provide a perforate surface formed by a plurality of parallel channels having a diameter (the lumen diameter of the fiber) of from about 30 to 65 microns. The fibers are cast at the surface 116 with a density of about 8,000 fibers per square inch.

As is shown in FIG. 2, the assembly 100 is disposed within the interface housing 72, and the cast sealing members 112 and 114 are seen to be cast in a manner so as to bond to the housing 72 at their outer perimeters. Thus, an aseptic seal is provided at either end of the housing with respect to the outer surfaces of the fibers 102. This aseptic seal is preferred due to the fact that as the nutrient solution proceeds through the lumens of the fibers 102, as further described, air or oxygen may be fed under adequate pressure through an inlet 130. Preferably, the hollow fibers 102 are produced from a material having a wall porosity sufficient to allow oxygen to pass through the cylindrical walls 104 in amounts which are sufficient to provide a proper level of oxygen in the nutrient solution yet is hydrophobic in order to resist the flow of liquid throughout the pores. Generally, a wall porosity of ranging from about 0.005 to about 0.1 microns in a polypropylene fiber material is appropriate for this purpose. The oxygen is seen to flow through the inlet 130 into the open spaces 132 within the housing portion 72 and between the seals 112 and 114. As is shown in FIG. 3, the hollow fibers between the seals 112 and 114 are unsealed and open to allow perfusion of the oxygen.

The nutrient solution is applied to the housing 70 by a solution inlet fitting 138, thereafter filling the internal area 140 within the end cap 86 and adjacent the sealing member 114. From this area, the nutrient solution may flow through the lumens 106 of the hollow fibers 102 toward the end 108 of the fiber assembly 100. While the nutrient solution may be drawn a short distance through the hollow fibers, as in the hollow fiber discs 28 described with respect to FIG. 1, the internal friction of hollow fibers having a length sufficient to permit membrane oxygenation, such as those shown in FIG. 2, require a positive hydraulic pressure on the nutrient solution to cause the solution to flow to the porous surface 118. Generally, with a hollow fiber assembly having a diameter of approximately 7 cm and an overall length between the surfaces 116 and 118 of about 14 cm, a hydraulic pressure of about 2 p.s.i. is sufficient to force the solution through the lumens to the surface 116.

In order to maintain proper pressure within the housing portion 72, or to determine and maintain appropriate temperatures of the growth solution, various apparatus such as the fitting 142, here shown to include a temperature probe 144, may be included in the housing 70.

Returning again to a description of the second housing portion 74, this portion is disposed at the distal end of the interface housing 70. As used herein the term distal, which is employed in the medical sciences to indicate a location remote from the point of attachment or origin, is used to describe a plant portion away from the center of the natural organism, e.g., the portion of a plant or shoot disposed in the direction of longitudinal growth. The term proximal is used to indicate a direction along the plant axis which is toward the origin of growth, for example, in natural plants the direction toward the roots.

A phloem sponge 150 is seen to be disposed at the distal end of the housing portion 72 and abutting the porous surface 116 of the hollow fiber assembly 100. This phloem sponge 150 is formed from a biocompatible porous substance having an open cell size and pattern which is neointimal with respect to plant tissue. The sponge 150 includes a plurality of projections 152, each having a central aperture 154 having an internal diameter of about 2 cm. According to the present invention, callus or explant tissue is inoculated onto the perforate surface 116 through the apertures 154, under clean room conditions. This tissue is indicated by the reference numerals 156 in FIG. 2. Thereafter, the housing portion 74 is secured and sealed to the distal end of the portion 70 by the bracket 76. The distal housing portion 74 is seen to be constructed from a rigid polymeric material forming a circumferential side 160, and a distal wall 162 including a plurality of apertures 164 which are disposed essentially coaxially with the projections 152 of the phloem sponge 150. The side 160 includes a circumferential external thread 165 which is disposed about the wall 162, and permits the attachment of a cover such as the cover 42 shown in FIG. 1.

A major portion of the interior of the portion 74 is formed from a molded, transparent, resilient and biocompatible polymeric material such as a room temperature vulcanization silicone polymer, indicated by the reference numeral 166. Preferably, a polymer which is compressible and extensible to the extent of radial limb growth is preferred so that support means for the growing limb or branch is provided. A room temperature vulcanization silicone product manufactured by Dow-Corning Medical Products and sold under the trademark Silastic Q 7-4840 medical grade liquid silicone rubber has been found effective for this purpose. This polymer may be molded into the portion 70, and includes recesses 168 which loosely mate with the projections 152, and a proximal surface 170 which abuts the phloem sponge 150. When the portion 74 is connected to the portion 72, sufficient space remains between the surface 170 and the perforate surface 116 to allow transfer of fluid by the sponge 150. Fluid which is exuded from the natural plant phloem is absorbed by the sponge 150, and may be removed through a port 172 which is sealed by a one-way valve 174 such as the duck-bill type valve shown in the drawing. The valve 174 permits draining of excess fluid while maintaining the aseptic environment for tissue growth.

Plant growth channels 176 are seen to extend from each of the recesses 168 through the polymer 166 to an outer or distal edge 178 of the housing portion 74. Upon attachment of the portions 72 and 74, and growth of the tissue 156, the shoots thus formed will grow distally through the phloem sponge apertures 154 and further through the channels 176. As the tissue 156 expands radially, it will grow into the phloem sponge 150. As the tissue 156 differentiates to form aerial plant portions, i.e., shoots, from the growth conditions, these shoots will extend longitudinally through the channels 176. As the shoots grow radially, the periderm tissue will bear against the walls of the channels 172 of the polymer 166, thus providing an aseptic seal for the shoot as it grows through the channel 176. This seal preserves the callus at the perforate surface 116, and prevents any degeneration of the enclosed shoot which may result from the perfusion of the nutrient solution beyond the callus tissue. Additionally, the polymer 166 provides support for the developing shoot. Additionally, as the shoot extends beyond the outer edge 178, the polymer 166 serves as a means for retaining the vascular system of the limb or branch in fluid communication with the perforate xylem surface 116 and the phloem sponge 150.

A wide variety of retaining means may be provided, depending upon the extent of plant growth required and the size of the generated limb. As is well known, a radially expanding plant stem generates force. The silicone polymer is preferred due to the fact that the polymer expands while maintaining sufficient compressibility to provide a support and sealing function to the limb. In the event less compressive force is desired, the polymer 166 may be formed with air bubbles immediately adjacent the channels 176 to lessen the initial resistance of the polymer to the radial expansion of each shoot. Further, if additional support is required, a biocompatible stainless steel wire screen mesh may be incorporated within the polymer 166 near the surface 170 through which the tissue and shoots must grow, thereby captivating the branches which will extend beyond the channels 176. Alternatively, the channels may be formed from or include a microencapsulated epoxy, including both catalyst and resin cells which rupture and reseal as the limb extends radially and distally to form an epoxy bond between the living portion and the polymer. Microencapsulated epoxy anaerobic resins used in this manner remain dormant until the crushing action between the limb and the limb retention housing causes the beads to burst and mix forming a region of cured epoxy resin of superior strength. A microencapsulated epoxy resin such as that sold by the 3M Corporation under the trademark Scotch-Grip 2353, commonly used for securing threaded fasteners, is preferred. A preferred use of microencapsulated epoxy resin precursors in connection with the limb retaining means is described in more detail with respect to FIG. 7(B).

Figure 6:
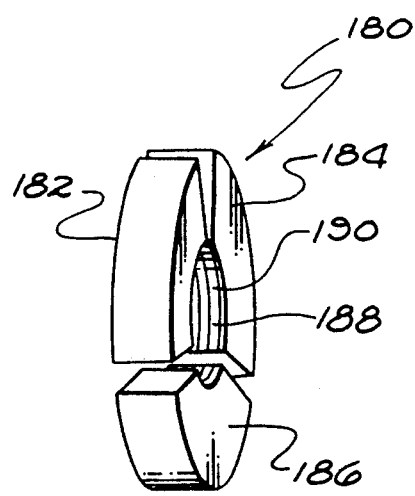
FIG. 6 is a perspective view of a limb retaining means described with respect to FIG. 2.

FIG. 6 details another form of retaining means which may be employed in the housing portion 74. Specifically, a disc member 180 is seen to be trifurcated into distinct sections 182, 184 and 186. Further, the member 180 includes an opening 188 which bears ridges and valleys 190 on the lateral surfaces thereof. When the polymer 166 is molded, the disc 180 may be disposed midway between the surfaces 162 and 170 with the channel 176 axially disposed through the opening 188 on the disc. As the shoot or limb which is formed within the channel 176 expands radially, the periderm contacts the ridges 190 to provide support and retention for the shoot, and as the limb expands further the individual sections of the disc member expand radially to accommodate limb growth. A plurality of disc members 180 may be provided around each of the channels 176.

Nutrient solutions and growth regulators which may be employed to develop the rootless vascular plants of the present invention are known in the art and, in particular, are described in the *Handbook of Plant Cell Culture*, Volumes I, II and III (MacMillan Publishing Co. 1984) which is incorporated by reference herein. In particular, the sections regarding organogenesis; embryogenesis; protoplast isolation and culture; and meristem, shoot tip and bud cultures describe basic techniques, nutrients and regulators of plant cell culture. In addition, sections which relate to the biochemical mechanisms of plant hormone activity describe the morphogenetic activities of the various phytohormones.

However, existing technology must be modified in several ways in order to optimize the growth of aerial plant portions on the artificial graft interface. First, it is preferred that any phytohormone or nutrient which stimulates root growth to the extent that growth of the aerial plant portions is inhibited should be avoided. Since root-inducing hormones are well known among those skilled in the art, the adaptation of existing nutrient solutions to this end can be attained without undue experimentation. In addition, it is preferable that steps be taken to eliminate or neutralize endotoxins which are produced by the plant and which are retained within the closed artificial vascular system. For example, the nutrient solutions described in the examples are seen to include about 0.18 weight percent polyvinyl-polypyrrolidone which has been shown to be effective in binding and neutralizing phenolic endotoxins produced by a variety of plants, thus allowing uninhibited growth. Third, it will be seen that the normal concentration of macroelements in known growth solutions is unnecessary, and often deleterious, to growth in the closed-system plant graft interface of the invention. For this reason, salts such as ammonium nitrate, potassium nitrate, calcium chloride, magnesium sulfate, potassium phosphate, chelated iron and sodium EDTA may be reduced to about ten percent of usual concentration to reduce vitrification.

Turning now to FIGS. 7, an embodiment will be described which permits the growth of shoots from explant tissue culture under clean room conditions which is then adapted to be used for the growth of branches in a natural environment. In that figure, an interface housing 200 includes a casing 202 formed from a transparent polymeric material. The casing 202 is seen to include a plurality of hollow fiber bundles 204 which extend longitudinally through the casing. Each end of the bundles 204 is embedded in a cast urethane sealing member embedded, respectively, within a distal end 206 and a proximal end 208 of the casing 202 in a manner which is essentially similar to the construction of the sealing members 112 and 114 shown in FIG. 2. In FIG. 7, however, the fiber bundles provide advantages in that the total number of fibers required is substantially less than the number required for the hollow fiber assembly 100 in FIG. 2, where the nutrient solutions are fed directly to the plant tissue by the fibers 100. The construction of these fiber bundles 204 is as described in detail with respect to FIGS. 3 and 5. The casing 202 is also seen to include an oxygen inlet 210 to enable membrane oxygenation of the nutrient solutions and a one-way valve similar to the valve 174 of FIG. 2, which is not specifically shown, is disposed toward the distal end 206 of the casing. The proximal end 208 includes threads 212 which are adapted to receive an end cap 214 which is attached to the casing 202 by the threaded collar 216. An aseptic seal at this proximal end is provided by the O-ring 218. The end cap 214 includes a thermocouple probe 220, a nutrient solution inlet 222, and a port 224 which is closed by a fitting 226. The port 224 allows access to the nutrient solution within the casing 202 for testing if desired.

The distal ends of the hollow fiber bundles 204 are seen, in combination with the cast sealing member which is similar to the member 112 in FIG. 2 but is not specifically shown by a reference numeral in FIG. 7, to form a perforate surface 228 which receives a lower retaining bracket 230. The bracket 230 is seen to include circumferential notches 232 which engage flanges 234 to prevent rotation of the lower retainer bracket within the casing 202 and to allow for peripheral drainage from the distal portion of the casing beyond the bracket 230. The bracket 230 also includes a plurality of apertures 236 and a central aperture 238 which mate, respectively, with each of the hollow fiber bundles 204.

Figure 7A:
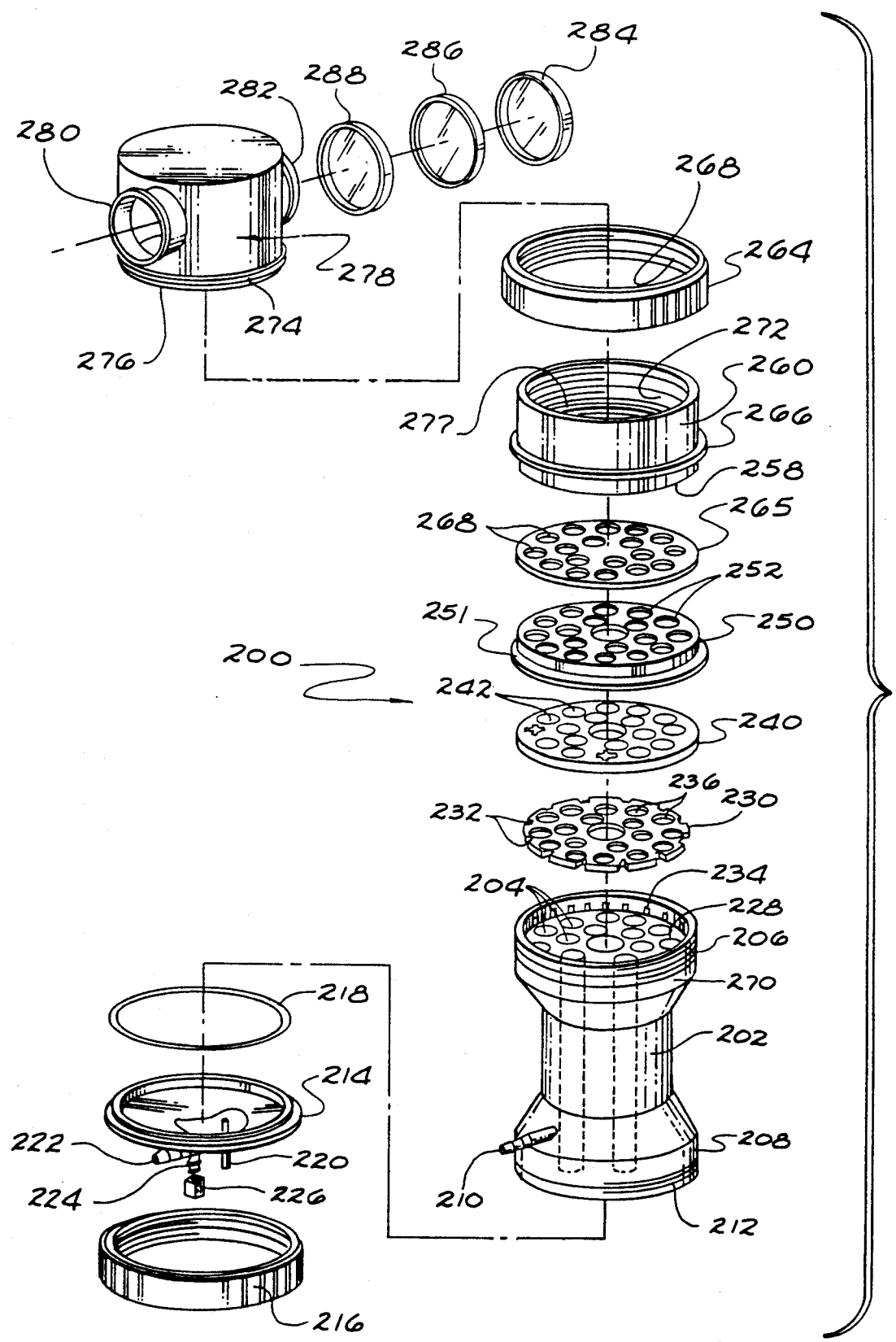
FIG. 7(A) is an exploded perspective view of an alternative embodiment of the systemic plant interface adapted for use in vitro or in field application.

It should be noted that the hollow fibers 204 in FIG. 7A are employed to permit membrane oxygenation of the nutrient solution, as the xylem interface is provided by fiber discs as later described. However, the housing 202 may be modified to permit plant growth directly from the fibers 204 in the manner described with respect to FIG. 2. In addition, the fibers 204 may not be employed and oxygenation provided by a sparging tube inserted within the casing in the manner described with respect to the interface shown in FIG. 1. However, in field operations it is generally preferred to employ the described membrane oxygenation construction as fluid transfer and the horizontal disposition of the casing are improved.

Above the lower retainer bracket 230 is a sponge member 240, including apertures 242 and 243, and a culture carousel 250, which also contains a plurality of apertures 252 which are coaxial with the hollow fiber bundles 204. The sponge 240 draws nutrient solution by capillary action from the phloem sponges later described.

When in assembled form, the bracket 230, sponge 240 and culture carousel 250 are secured to the casing or housing 202 by the abutting lower edge 258 of a second housing portion 260. The assembly of the above-mentioned apparatus, including the positioning of an upper retaining bracket 265 within the housing portion 260, will be described in more detail with respect to FIGS. 7(B) and 7(C). However, with respect to the construction of the interface housing 200 in general, the second housing portion 260 is secured to the casing 202 by a collar 264 which bears on a flange 266. The collar 264 includes internal threads 268 which engage external threads 270 of the casing 202. Internal threads 272 of the housing 260 engage with external threads 274 at a lower or proximal edge 276 of a cover 278. An internal annular flange 277 serves to secure the upper retainer bracket 265, as is shown in more detail in FIG. 7(C).

In FIG. 7(A), the cover 278 is seen to include ports 280 and 282, which are adapted to receive caps of various gas/water vapor permeability. These caps are serially engaged and removed as shown in FIG. 1. For example, the cap 284 may be nonpermeable to such vapor and thus useful in retaining high humidity conditions during the initial growth of the shoots as hereinafter described. A second cap 286 is semipermeable to gas/water vapor so that the developing shoots may be hardened, during growth, toward natural humidity. The cap 288 is totally permeable and is used in the final growth process prior to removal of the cover 278.

Figure 7B:
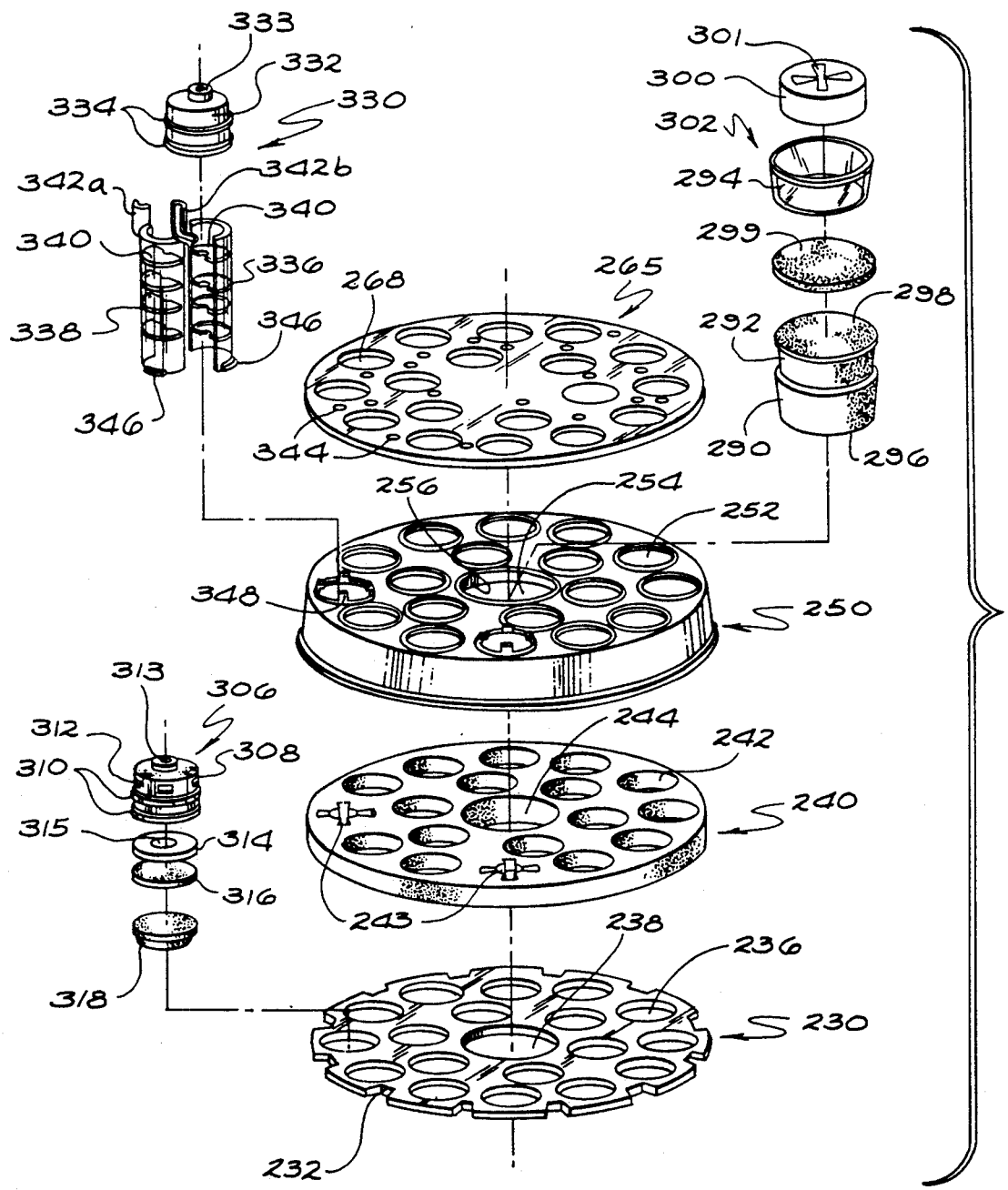
FIG. 7(B) is an exploded perspective view of the xylem-phloem interface and limb retention apparatus of the interface shown in FIG. 7(A)
Figure 7C:
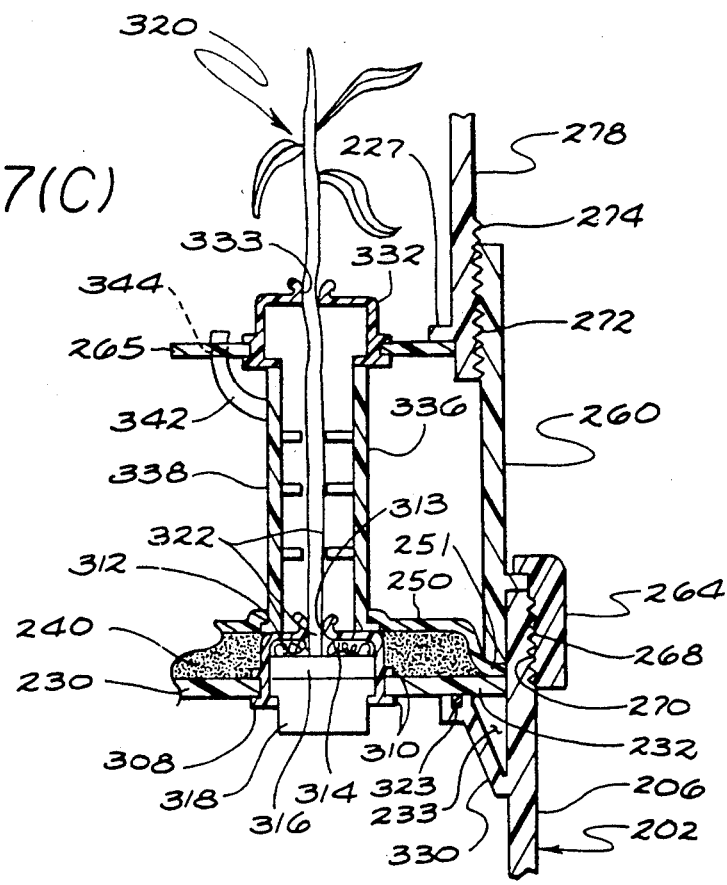
FIG. 7(C) is a cross-sectional view of a rootless shoot growing in the interface shown in FIG. 7(A)

Turning now to FIGS. 7(B) and 7(C), the construction and use of the interface housing 200 will be described in more detail. In FIG. 7(B), the lower retainer bracket 230, drain sponge 240, culture carousel 250 and upper retaining bracket 265 are shown. The lower bracket 230 includes, in addition to the apertures 236, at least one aperture 238, here shown to be centrally located and larger in diameter, for purposes which will later be described. Similarly, the sponge 240 includes a central aperture 244, and the culture carousel 250 includes a central aperture 254.

The central apertures are adapted to receive a feed sponge 290 having a groove 292 which receives a bottomless retainer cup 294 which, in turn, rests within the aperture 254. When the apparatus 302 is thus assembled and inserted, the sponge 290 mates with the edge of the aperture 244 in the phloem sponge 240. A lower edge 296 of the sponge 290, when fully inserted in the assembly, abuts the central hollow fiber bundle 204 and receives solution from the perforate surface thereof. The sponge 290 is seen to include a top surface 298 which receives a hollow fiber disc 299 which is similar to the disc 28 shown in FIG. 5. As described, the bottomless retainer cup 294 abuts the top of the disc 299, and rests within and is restrained from lateral movement by the edge 256 of the carousel central aperture 254. A neointimal phloem sponge 300, having an aperture 301, rests within the retainer cup 294 atop the disc 299. The apparatus indicated by reference numerals 294–301 is collectively referred to as a tissue culture apparatus 302.

The small apertures 236 and 242 are shown to be adapted to receive a shoot growth apparatus 306 which comprises a silicone rubber cap 308 having upper and lower circumferential flanges 310 and a plurality of openings 312. A neointimal phloem sponge 314 having a central aperture 315 is inserted into the cap 308 so that the sponge 314 protrudes, in part, through the openings 312. Directly below the sponge 314 is a hollow fiber disc 316, and thereafter a feed sponge 318.

Turning now to FIG. 7(C), a cap 308 is seen to be disposed with the flanges 310 above and below the lower retaining bracket 230. The feed sponge 318 is seen to protrude below the bracket 230 and positioned so as to contact the fiber bundle 204 which, although not shown in FIG. 7(C), lies directly below each of the shoot growth apparatus 306. The feed sponge 318 is seen to be positioned to feed nutrient solution to the hollow fiber disc 316, where it is transported by capillary action to a shoot 320 which is seen to be growing from the fiber disc 316 in the absence of root formation. A proximal portion 322 of the shoot 320 is seen to have grown and expanded radially on the disc 316 within the aperture 315 of the phloem sponge 314, and the natural phloem tissue has expanded radially and grown into the artificial phloem sponge 314. Natural phloem fluid exuded by the shoot 320 is thus conducted by the porous sponge 314, and thereafter to the sponge 240 and drained through the notch 232 into a cavity 233 and thereafter from the casing 202 as described with respect to FIG. 2.

In FIG. 7(C) the lower retaining bracket 230 is seen to be supported by a bracket 330 extending internally from the distal end 206 of the casing 202, and is sealed against the bracket 330 by an 0-ring 323 therebetween.

Returning to FIG. 7(B), a shoot-retaining means 330 is shown, which includes a silicone cap 332 which is similar to the cap 308 described above in that it includes upper and lower circumferential ridges 334, but the cap 332 does not include lateral openings 308. The cap 332 accepts the upper edges of mating support fittings 336 and 338 as is shown more clearly in FIG. 7(C). The fittings 336 and 338 are seen to include a plurality of shoot-support plates 340 which, when the fittings 336 and 338 are combined, form a series of longitudinal apertures which support the length of the shoot. The fittings also include upwardly extending arms 342a and b which, when the fittings are combined, form an upwardly extending hollow arm 342 which is inserted through one of the plurality of apertures 344 in the upper retaining bracket 265. The fittings 336 and 338 also include twistlock flanges 346 which enable the fastening of the shoot support means 330 to the culture carousel by engagement with the twistlock receiving brackets 348 on the carousel 250.

In use, the systemic plant interface of this embodiment is initially employed to glow a number of small shoots from tissue culture, followed by the dissection of individual shoots which are then inserted into the separate shoot growth apparatus and shoot retaining means to permit the further growth of the initial shoots to form branches. Initially, the casing 202 with the end cap 214 attached is placed in a vertical position, and the lower retaining bracket 230, sponge 240 and culture carousel 250 are sequentially inserted atop the perforate surface 228 as described, and are secured to the casing 202 by the pressure of the housing portion 260 on the flange 251 of the carousel 250. The sponge 290, disc 299 retainer cup 294 and phloem sponge 300 are then inserted through the central apertures 238, 244 and 254, and appropriate callus or explant tissue is then seated within the aperture 301 atop the disc 299. Thereafter, the cover 278 is attached to the top of the housing 260. Appropriate growth solution is then introduced through the inlet 222 through an exterior fluid level control to maintain the solution at the level of the surface 228, until a plurality of shoots form in the plant tissue. It should be noted that the growth of plant tissue culture requires that the tissue be initially loaded, and grown, under clean room conditions to prohibit bacterial growth and contamination of the nutrient solutions and tissue.

When the individual shoots have extended longitudinally to a length of about 80 mm the cover 278 is removed under aseptic conditions and the individual shoots are cut from the explant tissue, and carefully inserted through the aperture 313 of the silicone cap 308 of the shoot growth apparatus 306 so that the excised tissue rests on the artificial xylem surface 316 within the phloem sponge aperture 315. The apparatus 306 has preferably been previously inserted into an aperture 236 of the lower retaining bracket 230, and the sponge 240 has been placed as is shown in FIG. 7(C) so that the walls of one of the apertures 242 abut the phloem sponge 314 within the apparatus 306. It should be noted that the apertures in the sponge 240 may assume a variety of shapes as long as communication with the phloem sponge 314 and drainage from the natural phloem of the shoot within the apparatus 306 is obtained to enable drainage of highly viscous photosynthates, e.g., isoprene compounds. For example, the silicone cap 308 may have openings 312 which allow insertion of the inwardly extending edges of an X-shaped aperture such as is indicated by the reference numerals 243, which may extend to the natural Phloem tissue. Following insertion of the apparatus 306 and placement of sponge 240, the culture carousel is then positioned as shown in FIG. (7C). It should be understood that the apparatus is equally adaptable to having each of the shoot growth apparatus installed prior to the growth of the explant tissue to form shoots, and the excised shoots may then be placed on the xylem discs 316 by widening the aperture 313 of the resilient cap 308 to insert the excised shoots therein.

Several techniques may be employed to initiate the growth of the callus or explant tissue on the artificial xylem fibers. The tissue may be placed directly to the hollow fiber discs 316. Alternatively, the tissue may be similarly applied to the fiber disc 299, and after shoots of acceptable dimensions are formed they may be excised and transferred to the individual discs 316. Alternatively, selected shoots from field plants may be obtained and disinfected, and then sealed at the point of incision with dental impression compounds or other appropriate material to inhibit air locking of the natural vascular system of the shoot. Under laminar flow/clean room conditions, shoots obtained in this manner have been further disinfected with a mercuric chloride solution (0.01M) for several minutes. Thereafter, these shoots were cut to acceptable dimensions and introduced into the individual shoot growth sites on the hollow fiber disc.

Following such insertion, the shoot support fittings are carefully placed around the shoot stem extending through the coaxial apertures formed by the plates 340, and the assembled fittings 336–338 are then engaged with the culture carousel 250 by the twist lock fittings 346 and 348. Preferably, the abutting portions of the fittings 336–338 are coated with microencapsulated epoxy resin prior to this assembly to bond the fittings into a rigid unit. Following such engagement, the silicone cap 332 is positioned atop the assembled fitting 336–338 with the shoot extending through the aperture 333. After each of the fittings 336–338 is attached to the culture carousel 250, and each of the caps 332 is placed thereon, the upper retaining bracket 265 is placed over the caps 332 between the flanges 334, with the arms 342 extending through the apertures 344 as is shown in FIG. 7(C). Alternatively, the entire apparatus 330 may be assembled and attached to the carousel 250, and the shoot may be inserted through the respective apertures of the apparatus until the proximal end 322 is seated within the aperture 315 atop the disc 316.

In order to provide for additional limb retention when the interface 200 is disposed in a horizontal position, RTV silicone rubber or other biocompatible polymers are introduced through the hollow arms 342 to fill the interior of the fitting 336-338. Further, the space surrounding the fittings 336-338 may be filled with such polymers to produce a limb support and retention means similar to that described with respect to FIG. 2. Thereafter, the cover 278 is again secured to the housing 200, with caps providing the appropriate permeability attached, and the interface housing 200 is charged with nutrient solution. After the contamination-free growth of all shoots has been confirmed, the charged housing 200 may be transferred to a natural environment for further growth. For example, hundreds of the interface housing units 200 may be supported by towers in either a horizontal or vertical position when the shoots 320 are sufficiently hardened to be exposed to ambient temperature and humidity. The growth solutions and oxygen circulation may then be manifolded with substantial economies of scale. It will be appreciated that each individual housing 200, in this embodiment, will enable the growth of eighteen separate plant product-bearing limbs.

The embodiment set forth in FIG. 7 is particularly advantageous due to the fact that when limb growth and support is completed or no longer desired, the portion distal to the surface 228 of the casing 202 may be removed and discarded and the components comprising the casing 202 may be reused for the growth of new limbs.

As the shoots 320 expand both radially and longitudinally during growth, additional retaining means may be provided. For example, the fitting 336-338 may be injected with RTV silicone or microencapsulated epoxy adhesive, and the space surrounding the fitting 336-338 may also be injected with similar material, producing a limb support and retention means similar to that described with respect to FIG. 2.

The embodiment described in FIG. 7(A) may be altered to provide for bubble oxygenation if desired. In such an apparatus, the hollow fiber bundles 204 may be omitted and a thin disc of longitudinal hollow fibers may be inserted at the distal end of the casing 202 solely to control the flow of solution to the artificial xylem discs. The nutrient solution flows through the inlet 222, with appropriate solution drainage means at the distal end, and the permeable oxygen sparging probe is inserted in the oxygen inlet 210 to oxygenate the solution without relying on the permeability of the hollow fiber bundle or bundles.

The use of the systemic plant interface of the invention in the growth of rootless, vascular plants will be described in the following examples.

EXAMPLE ONE

A variety of shoots of various plant species have been grown in a systemic plant interface such as that shown in FIG. 2. In each such trial, a variation of the known Linsmaier-Shoog growth medium was employed. However, the traditional formulation of this medium was modified for use in the closed-loop system by reducing a proportion of macroelements to reduce vitrification, and including an endotoxin-inhibiting formulation. While a wide variety of endotoxin-binding agents may be employed, polyvinyl-polypyrrolidone in concentrations of from about 0.05 to about 0.2 weight percent are effective for this purpose.

In an initial trial, a field shoot obtained from a Mission fig tree (Ficus carica) was excised and the proximal end of the shoot was applied to the perforate surface 116 of the housing 70 through one of the channels 176 and apertures 154. When inserted into the housing, this shoot had a diameter of about 3 mm and a length of about 85 mm. The apparatus 70 was then mounted in a horizontal position in a supporting yoke, and the nutrient solution shown in Table 1 was recirculated into the housing 70 through the solution inlet fitting 138. The solution migrated through the hollow fibers 100 under a pressure of 2 p.s.i., which was produced by a positive pressure of sterile nitrogen in the vessel containing the nutrient solution. The solution was absorbed by the phloem sponge 150, delivered to the xylem interface and transferred to the natural xylem of the plant. Excess solution, photosynthates and endotoxins from the plants exited from the housing 70 through the valve 174. The flow of the nutrient solution through the housing occurred, under these conditions, at less than 6.5 milliliters per minute.

Since the solution exiting the housing 70 through the valve 174 included photosynthates and endotoxins produced by the growing plant, this solution was passed through a resin column to assist in the extraction of the endotoxins (primarily phenolics) after which the solution was filtered through 0.45 and 0.2 micron filters in series and returned to the initial pressurized vessel. During the growth process, ten percent of the solution was removed and replaced with freshly mixed growth solution every seventy-two hours.

During a period of ten weeks, the Mission fig branch was allowed to grow. During this time, a cover similar to the cover 278 in FIG. 7(A) remained in place to provide proper humidity for the growing shoot. After the end of ten weeks, the shoot had grown from 85 mm to 100 mm in length and exhibited new leaf growth. At the end of the ten week initial growth period, the protective cover was removed and within five weeks the branch had reached a length of 135 mm, and additional leaf growth had occurred.

EXAMPLE TWO

In addition to the subgrowth of plants in the subtropical category (Mission fig), plants of the citrus variety were also grown. Tissue culture from the Carrizo and Swingle orange were obtained, and pressed onto a hollow fiber disc such as that indicated by the reference numeral 298 of the tissue culture apparatus 302 as shown in FIG. 7(B). After a period of about four weeks, shoots having a length of about 80 mm were excised, and inserted into the housing 70 as described. The nutrient solution was then circulated with the protective cover in place, and after eleven weeks the shoots had reached a length of 90 mm. After removal of the protective cover, the shoots continued to grow for a period of four weeks to a length of 95 mm. New leaf growth was exhibited during this period.

Further with respect to the citrus family, a Swingle orange shoot was grown from callus tissue, inserted into the housing 70, with results identical to that described for the shoots initially grown from tissue culture. Also, field shoots from the Pink Grapefruit variety were excised, disinfected and grown with similar results in the absence of roots.

EXAMPLE THREE

In addition to plants of the citrus family, plants of the malus family have also been grown. MacIntosh apple shoots, obtained from the growth of tissue culture, were inserted into the housing 70 and grown over a period of twenty-seven weeks. In the initial stages, the shoots grew from an initial length of 90 mm to a length of 95 mm with the protective covering in place over a period of twenty weeks. Following the removal of the protective cover, the shoots extended to a length of 110 mm over a period of seven weeks. In a similar manner, Jonathan apple shoots were isolated from tissue culture and grown in the housing 70, in the absence of roots, for a period of twenty-nine weeks.

EXAMPLE FOUR

Further, plants from the Prunus family were also grown from tissue culture in the manner described in Example Three. Shoots from the Colt cherry, Suncrest peach and Myrobalan plum were grown from tissue culture on the perforate surface provided by the artificial xylem discs described above, inserted into the housing 70, and grown over a period of twenty-five weeks. The Cherry Colt shoots initially were inserted into the housing 70 at a length of 90 mm, and grew to a length of 100 mm within this time period. The Suncrest peach shoots grew from 105 mm to 125 mm during this time. In each instance, the protective cover was left in place until the last eight weeks of growth.

In an alternative embodiment, apparatus Which is useful in the propagation and growth of tissue culture is provided. Specifically, artificial plant interface is employed in a method for preparing rooted plantlets for transfer to a natural environment.

A growth chamber for a vascular plant having xylem and phloem tissue is described, which comprises a container supporting an artificial xylem surface formed from a plurality of hollow fibers, each having a lumen and an outer surface. The proximal ends of the fibers are bonded to each other at the other surfaces, and having open lumens to form a perforate artificial xylem surface. This surface is supported within the container such that a second or distal end of the fibers extends into a chamber adapted to contain a nutrient medium. The container also includes an absorptive neointimal phloem interface disposed adjacent the xylem surface, and means for providing a flow of rinse solution through the phloem interface.

Means for the inlet and outlet of both the nutrient medium and the rinse solution may also be provided, and preferably both of said outlets include means to inhibit the passage of pathogenic substances such as bacteria, fungus and viruses from the container to isolate contamination.

The container may be used in a method for propagating plant tissue and growing vascular plants having xylem and phloem tissue. The method comprises placing a totipotent plant cell or explant tissue on the artificial xylem surface described above, the plant cell or tissue being placed on the surface in fluid communication with the absorptive phloem interface, and caused to grow by applying nutrient media into the nutrient media chamber, through the lumens to the plant tissue. Preferably, the method includes rinsing accumulated phytotoxins from the phloem interface with a rinse solution, which preferably is isotonic with respect to natural fluids within the growing tissue.

Figure 9A:
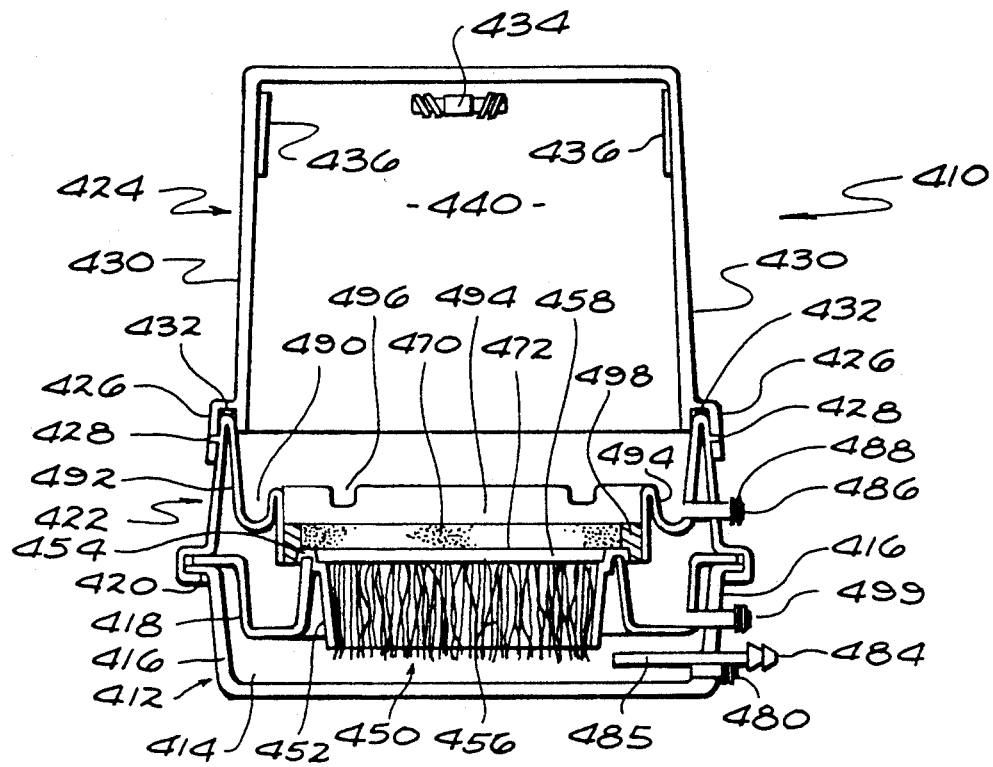
FIG. 9(A) is a schematic cross-sectional end view of a chamber for propagating plant cells or explant tissue to form viable shoots.
Figure 9B:
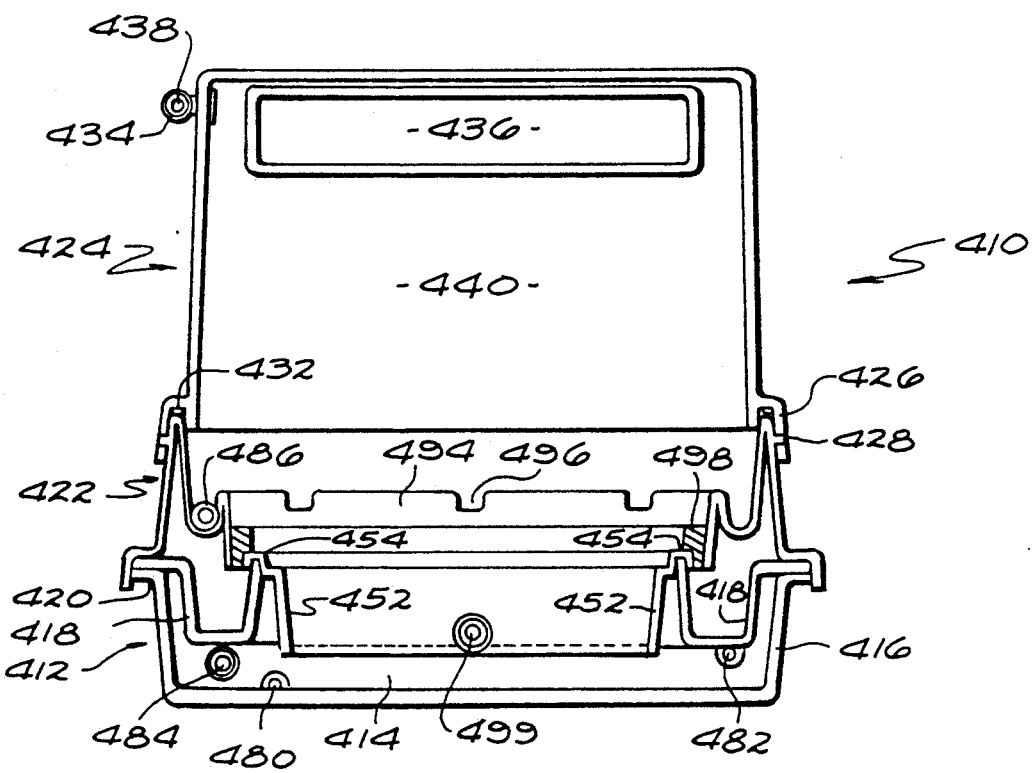
FIG. 9(B) is a schematic cross-sectional side view of the propagation chamber shown in FIG. 9(A)
Figure 9C:
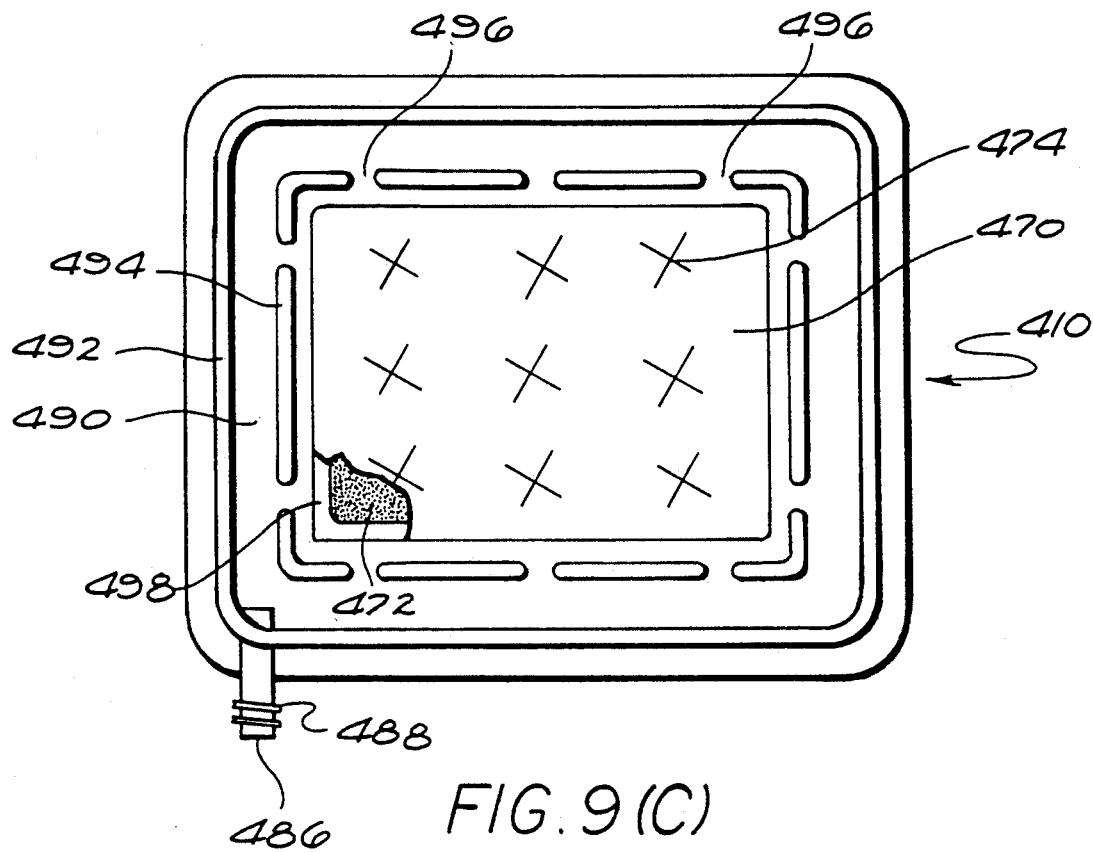
FIG. 9(C) is a schematic top view of the shoot propagation chamber.

A propagation chamber constructed in accordance with the invention is shown in FIGS. 9(A)-9(C) as designated by the reference numeral 410. The chamber 410 may be constructed from a variety of resinous or ceramic materials, but preferably is molded from a high impact polystyrene or polycarbonate material which will withstand the repeated autoclaving required by tissue culture techniques. The chamber 410 is seen to include a lower tray 412 which forms a reservoir or chamber 414 for the containment of a nutrient medium as later described. The lower tray 412 is seen to include tapering sides 416 supporting a rinse solution receiving tray 418, which rests on supporting flanges 420 of the tray 412. Disposed above the tray 418 is an upper support tray 422, which is seen to enable the lower tray 412, the rinse solution receiving tray 418 and the upper support tray 422 to be joined as a unitary member by rolling the lower edge of the tray 422 beneath the flange 420 after softening the lower edge with a heat-sealing means.

A transparent top cover 424 is attached to the upper support tray 422 by lower flange portions 426 which engage latch members 428 that are formed on the external surface of the upper support tray 422. The sides 430 and flanges 426 of the top cover 424 form a recess (not bearing a specific reference numeral) which receives an 0-ring 432 to form an air-tight and aseptic seal between the top cover 424 and the upper tray 422.

The top cover 424 is also seen to include a carbon dioxide inlet 434, and microbial shield-water vapor diffusion membrane means 436, which may be adapted to and employed for the purposes described with respect to the ports and caps 280-288 as shown in FIG. 7(A). In this embodiment, the membrane 436 provides significant advantages in that it permits gas transfer without the introduction of microbial contamination into the propagation or growth chamber. In addition, the membrane reduces stress on the cover and cover seal during autoclaving. This vapor diffusion membrane means provides significant advantages in any chamber which is employed for the growth of plant tissue in a sterile environment in the presence of a nutrient medium. Such chambers unavoidably require the inlet and egress of gases and water vapor due to temperature changes in the surrounding environment. A significant improvement is provided through the inclusion of a vapor diffusion membrane means having a porosity which permits the passage of gases and water vapor and inhibits the passage of pathogenic substances into the chamber. Generally, a porosity of about 0.2 microns is sufficient to inhibit the passage of virus, bacteria and fungus through the membrane, but as the thickness of the membrane increases the porosity may increase up to about 60 microns if a sufficiently convoluted pathway through the membrane is provided. Preferably, a membrane formed from a blend of high density and ultra high molecular weight polyethylene, having random pores of from 0.45 to 60 microns, functions as a "depth filter" and is sufficient for preventing the passage of most pathogenic substances. Similar material may also be employed in the membranes 50-54 and 284-288 described with respect to FIGS. 1 and 7(A).

The carbon dioxide inlet 434 is seen to have a longitudinal bore 438 in addition to a transverse bore leading to the growth chamber 440 within the chamber 410, to enable the feed of carbon dioxide to a plurality of the propagation chambers in parallel, with a carbon dioxide atmosphere being maintained within the growth chamber 440 under positive pressure.

An artificial xylem member 450 is supported within the lower tray 412 by a supporting collar 452 which engages the internal edges of the receiving tray 418 by flanges 454. The xylem member 450 includes a plurality of hollow fibers 456, which are sealed at a proximal end in a cast sealing member 458 in a manner similar to that described with respect to FIG. 4. However, in this embodiment the distal ends of the fibers are not restrained by a cast medium. The fibers 456 will be described in more detail in the description of FIG. 10. From a top view as shown in FIG. 9(C), the cast sealing member 458 is seen to comprise a rectangular perforate or artificial xylem surface.

Figure 10:
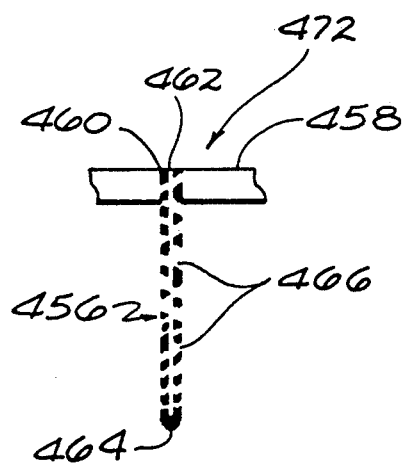
FIG. 10 is a schematic cross-sectional side view of the hollow fiber configuration employed in the embodiments set forth in FIGS. 9 and 11.

In FIG. 10, the artificial xylem surface 458 and one of the fibers 456 is shown in a figurative cross-sectional view. The proximal end 460 of the fiber is seen to have an open lumen 462, while the distal end 464 is seen to have an end which is heat sealed. The fibers 456 are made from materials described with respect to the fibers 102, but in preparing the xylem member 450 the fibers are first heat sealed at both ends, and then the proximal end is sealed in an appropriate casting resin. Subsequently, a transverse cut is made across the cast member to form a planar surface having a plurality of open lumens from the fibers. This method of forming an artificial xylem surface and fiber assembly is also adaptable to form the hollow fiber assembly 100 described in FIGS. 2 and 3.

The hollow fiber 456 has a lumen diameter of up to about 120 microns, and is shown to have transverse channels 466 which indicate a porosity of from about 0.01 to 0.45 microns. The fibers are preferably made from a hydrophilic resinous material, and the hydrophilic porosity provided by the channels 466 permits the influx of fluid, i.e., nutrient solution, which is then transported by capillary action to the proximal end 460, that is, the surface of the artificial xylem means 458.

Returning to FIGS. 9, an absorptive phloem interface 470, such as a neointimal sponge, is disposed adjacent a proximal surface 472 of the artificial xylem member 450.

In use, a plurality of totipotent plant cells or explant tissue is inserted through incisions 474 in the phloem sponge 470 and placed on the artificial xylem surface 472. The plant tissue is thus capable of seating on the surface 472 and forming xylem tissue in fluid communication with the lumens 462, and is also capable of fluid communication with the phloem interface sponge 470.

The plant tissue then begins to propagate as described above, eventually forming a plurality of shoots which extend through the incisions 474 above the sponge 470 into the growth chamber 440.

To encourage such growth, nutrient solution is applied to the chamber or reservoir 414 through a medium inlet 480. The medium fills the reservoir 414 to the level of a medium outlet 482, which is seen to be of a height which is sufficient to allow the distal ends of the fibers 456 to extend into the nutrient medium. Preferably, the flow of medium through the outlet 482 is partially blocked with a porous plastic filter which inhibits the flow of contaminating particulate or pathogenic material such as bacteria or viruses. This is done to isolate any contamination which would otherwise be introduced into other chambers during use. During the circulation of the nutrient medium, oxygen may be introduced through a sparging inlet 484 into a sparging tube 485 if desired.

At appropriate times during the propagation of the tissue, an isotonic, sterile rinse solution may be introduced into the chamber 410 through a rinse solution inlet 486 which is seen to include threads or flanges 488 for the attachment of the fluid delivery tubing, as are all the fluid inlets and outlets described herein. Preferably, the rinse media is a sterile, deionized aqueous solution adjusted to the physiological pH of the plant, but any solution which is isotonic and capable of removing endotoxins or waste material exuded by the plant tissue into the phloem sponge is acceptable.

The rinse solution flows through the inlet 486 to a valley 490 which is formed between internal side walls 492 and 494 of the upper support tray 422. The valley 490 is seen to be generally rectangular in FIG. 9(C), and the rinse solution thus courses through detents 496 in the internal side wall 494 onto the sponge 470, where it flows by gravity through a porous plastic collar 498 into the rinse solution receiving tray 418. From the tray 418, the rinse solution exits the chamber 410 through a rinse solution outlet 499 which is equipped with a porous plastic filter to isolate the chamber 410 in a manner similar to that described with respect to the medium outlet 482. The plastic collar 498 has a sufficient porosity to regulate the flow of fluid through the neointimal sponge 470, and preferably has a porosity of about 10 microns.

In practice, explant tissue having a diameter of about 7 mm is placed on the xylem surface 472 through the incisons 474, and a nutrient solution allowed to flow through the chamber 410 is described. Within two to three weeks, at least 100 multiple shoots grow from each tissue explant. These shoots may then be excised with a scalpel and transferred to a growth chamber, such as is shown in FIG. 11(A) and (B), for further propagation. After the shoots have been excised from the explant tissue grown in the chamber 410, the growth conditions may be maintained and the tissue will repeatedly generate shoots until so much callus is formed on the tissue that further shoot growth ceases. As many as 20-25 repeated shoot growths may be sustained from a single tissue explant when propagated with the apparatus and method described.

When the shoots in the propagation chamber 410 have grown to about the size of toothpicks, individual shoots may be excised from the explant tissue with a scalpel and transferred to a growth chamber 510, as described with respect to FIGS. 11(A) and (B). The growth chamber 510 is not dissimilar to the propagation chamber 410, in that it is constructed of resinous material, preferably polystyrene or polycarbonate resin, which will withstand repeated autoclaving. The chamber 510 includes a lower tray 512, forming a nutrient solution containing reservoir or chamber 514 contained in part by sides 516, and a rinse solution receiving tray 518 which also serves a support function as hereinafter described. The tray 518 is attached to the sides 516 by resting on a flange 520 and a heat sealed edge 521 of an upper support tray 522.

In turn, the tray 522 supports a top cover 524 which is attached by flanges 526 which engage latch members 528 which depend from a side 530 of the top cover. An 0-ring 532 is seen to seal the top cover 524 to the upper support tray 522.

Similar to the propagation chamber 410, the top cover 524 also includes a $CO_2$ inlet 534 and vapor diffusion membrane means 536. The $CO_2$ inlet 534 is also seen to include a longitudinal bore 538 for purposes described in the description of FIG. 9.

The chamber 510 includes individual receptacles 540. In this embodiment, fifteen such receptacles are provided, each formed by molded peaks 542 in the upper support tray 522.

The receptacles 540 are each adapted to retain an artificial xylem member 550 which is retained by a supporting collar 552 which engages a flange 554 on the receiving tray 518. The xylem member 550 includes fibers 556 and a cast sealing member 558 which provides a proximal surface 560 which includes open fiber lumens similar to those described with reference numeral 462 in FIG. 9. The fibers 556 may be identical, except as to the overall dimension which will be apparent in the drawings, to those described in FIG. 10.

Each receptacle 540 is also adapted to receive, disposed above the xylem member 550, a supporting absorptive phloem interface collar 570 which is adjacent a perforate xylem surface 572 of the xylem means. The neointimal sponge 570 is laterally enclosed by a porous plastic cincture 573 which abuts side walls 574 of the receptacles 540. The phloem sponge 570 is enclosed at an upper edge by a retention seal 576, and includes a slot 578 which facilitates insertion of shoots as hereinafter described.

The growth chamber 510 is adapted to employ nutrient and rinse solutions in a manner similar to that referred to above with respect to the propagation chamber 410, and thus includes a growth medium inlet 580, a nutrient medium outlet 582 which is detailed in FIG. 11(B) but not specifically shown in FIG. 11(A), and an oxygen-sparging inlet 584 which communicates with a sparging tube 585.

Further, and for purposes described with respect to the propagation chamber 410, the growth chamber 510 includes a rinse solution inlet 586 which is seen to include, as do all fluid inlets and outlets in this Figure, flanges or threads 588 for the connection of tubing or the like. The rinse solution inlet 586 provides for the flow of solution to a plurality of valleys 590 formed by side walls 592 and 594 of the upper support tray 522.

The construction of the growth chamber 510 is best understood in terms of the method for growth of shoots therein. Shoots from the propagation chamber 410 are excised from the growing tissue when the shoots have attained approximately the size of toothpicks. After being excised with a scalpel under sterile conditions, the shoots are inserted into the phloem sponge 570 through the slot 570, extending about 2 mm beyond the bottom of the sponge, and the phloem sponge is then inserted into the porous cincture 573 and secured into one of the receptacles 540 with the lower end of the shoot abutting the artificial xylem surface 572.

After the installation of the fifteen shoots and the closing of the top cover 524, nutrient solution is applied to the chamber or reservoir 514 through a medium inlet 580. The medium fills the reservoir 514 to the level of a medium level 582, which is seen to be of a height which is sufficient to allow the distal ends of the fibers 556 to extend into the nutrient medium. The hydrophilic porosity provided by the channels 446 of the fibers 556 permits the influx of fluid, i.e., the nutrient solution, which is then transported by capillary action to the proximal end or top 572 of the artificial xylem means 558. Alternatively, the non-porous fibers described above may be employed in the chambers 410 and 510.

Preferably, the flow of medium through the outlet 582 is partially blocked with a porous plastic filter which inhibits the flow of contaminating particulate or pathogenic material. Plant hormones known as "pulsing" agents may be added to both the nutrient and rinse solutions to induce the preferred aspects of plant growth.

As set forth, the isotonic rinse solution is caused to flow into the valleys 590. It should be understood that the support tray 522 is essentially rectangular, and includes communicating longitudinal and transverse valleys. The rinse solution flows through the valleys to a level which causes the solution to flow through the detents 596 which are disposed on either side of the individual receptacles 540. This rinse solution then flows through the phloem sponge 570, by the force of gravity, and exits through the porous cup 572. Thereafter, the rinse solution collects at the bottom of the rinse solution receiving tray 518 and exits the growth chamber 510 through the rinse outlet 599.

In this aspect of the invention, the use of root-growth hormones in the nutrient solution in the growth chamber 510 provides significant advantages in a method for plant propagation. After obtaining a shoot grown from vascular plant tissue, placing the shoot in the supporting, biocompatible and absorptive collar 570 which provides fluid communication with the phloem tissue of the shoot, applying liquid nutrient media to the plant and inducing lateral root growth from the shoot into the supporting collar; the shoot and collar may be planted in a soil-like medium for further growth. A variety of solid or soil-like media may be employed, such as vermiculite or a wide variety of other potting mixes.

Specifically, the shoot grows vigorously on the artificial xylem surface 572, due to the fact that the xylem tissue is in communication with the artificial xylem fibers. At an appropriate stage of shoot growth, root-growth hormones induce the lateral formation of roots, which grow into the phloem sponge 570. When the shoot and the root formation is of sufficient size and is physiologically prepared for existence in a natural environment, the shoot may be easily removed from the growth chamber 510 and the xylem surface 572, as the roots by this time have begun to sustain the vascular flow within the plant. While the plant tissue has been intimate with the hollow fibers on the artificial xylem surface, the removal of the plant from that surface does not severely injure the shoot or affect its further growth.

After removal from the chamber, the established shoots may be planted, along with the sponge 570, in potting mix and will develop rapidly into mature plants.

This method of propagating tissue culture into mature plants provides substantial advantages. First, through the use of the artificial xylem and phloem system during the initial growth of the shoots, survival is substantially improved. The artificial root system and the hydrophilic hollow fiber allow for a microbial shield while permitting nutrients to flow to the tissue as needed. In addition, the rinse system may be automated and conducted in parallel for a large number of individual chambers, thus eluting plant endotoxins and greatly increasing the survival of the shoots. This type of rinse system has been impossible with previous propagation methods, which rely on the formation of roots in agar and inhibit nutrient flow and plant growth prior to root formation. Further, it has been found that superior shoot growth is obtained through the maintenance of lower humidity in the propagation and growth chambers. However, it is difficult to obtain low humidity in existing chambers since the agar medium dries and cracks under these conditions. In contrast, the use of the described artificial xylem interface allows the accelerated growth of shoots under low humidity conditions.

In an alternative embodiment, a portable systemic xylem interface is provided which enables the unitary transfer of the growing shoot and the supporting interface to a new environment. As used with respect to this embodiment, the term "portable" refers to a plant-supporting xylem interface which is removable, along with the plant, from the propagation vessel.

As is shown in FIG. 12, a systemic interface, including a body portion; an artificial surface, including perforations, which is capable of mating with natural xylem tissue and transferring nutrient solution thereto; and wicking means in contact with the perforate surface. The interface, which is in some respects a mechanical fastener, is designated by the reference numeral 610. The fastener 610 is preferably formed from a resinous material, and most preferably is formed from an autoclavable material such as a polycarbonate resin if repeated usage is desired. The fastener 610 is seen to include a lower body portion 612 and an upper body portion 614. The portion 614 is seen to comprise a basin-like member 616 which is essentially circular from an overhead view. The basin is seen to contain a wicking sponge member 618 which is preferably formed from an autoclavable material (i.e., an open-cell material wherein the open-cell or sponge-like nature is not destroyed by the heat required to sterilize the fastener). While a neointimal sponge material such as that employed in the artificial phloem is not required, the Merocel sponge has been found advantageous for this use. However, any material which provides the capillary dispersion of fluid, as described, may be employed.

The sponge 618 is seen to contact a perforate surface 620 which provides the artificial xylem surface of the interface 610. The surface 620 may be formed from discs of hollow fibers such as that shown in FIG. 5, or may be formed from capillary-pore membrane laminates such as those sold by the Nuclepore Corporation. These are polyester or polypropylene films, or laminates of both such polymers, which are exposed to sufficient X- or other radiation, or other means, to form a perforate surface which is capable of mating with natural xylem tissue. A Nuclepore or similar film having perforations of about 0.2 micron and a perforation density of about $3 \times 10^8$ perforations/cm$^2 \pm 15\%$ has been found to be advantageous in that it mates with natural xylem tissue and also serves as a barrier to pathogens.

Any of the perforate surfaces which are employed to form the surface 620 may be sealed inside the top of the side walls 622 of the basin 616, as shown in FIG. 12, with silicone or other appropriate adhesives, or a more pliable perforate surface such as the Nuclepore material may be wrapped or formed around the outside edges of the side wall 622.

The lower portion 612 is seen to comprise a sheath-like cylindrical casing 624 which surrounds a plurality of hydrophilic, e.g., surfactant-treated, hollow fibers 626 similar to the fibers 456 in FIGS. 9 and 10, which are seen to extend upwardly to contact the sponge 618. The casing 624 includes openings 628 to permit the flow of medium around the fibers 626, as described.

The fibers are seen to be engaged, at the lowest portion of the casing 624, in a sealing member 630, i.e., a plug formed from appropriate material which captivates the fibers at the lower end of the casing 624. In a similar plug 632 captivates the fibers at an upper end of the casing 624, that is, where the casing 624 joins with the basic 616. These plugs, which may be formed from a urethane resin or by a heat sealing means, captivate the fibers so that fiber shrinking does not occur during autoclaving. Since the shrinkage will reduce both the pore and lumen size of the fibers, such sealing at both ends of the casing 624 is preferred. If, however, autoclaving is not anticipated then the lower plug 630 may be omitted. The upper plug 632 also serves to limit the flow of nutrient solution to that which wicks through the fibers 626, as more fully described in the description of the use of the interface 610.

Virtually any number of fibers may be disposed within the interface 610, with the limits being established by the need for sufficient capillary profusion to the sponge 618, and the cost of the fibers. Generally, about four to eight fiber strands each having a sufficient lumen diameter and wall porosity are preferred. The sufficiency of the lumen diameter is established by the ability of the fibers to wick the fluid to the sponge 618. The sufficiency of the wall porosity is determined by the ability of the fibers to serve as a barrier to the porosity of 0.2 micron will serve as a barrier to the flow of most pathogenic agents. It has been found that five or six fibers having a lumen diameter of 100–200 microns, and a wall porosity of about 0.2 micron will provide filtration through the fiber walls and permit wicking, i.e., capillary transport, of nutrient medium to a height of about 5½ inches.

In FIG. 12, the fibers are seen to be looped from the sponge 618 to the plug 630, and then returned to the sponge. Alternatively, individual lengths of fibers may be employed. A wide variety of automated methods may be employed to manufacture the interface 610, and the fibers may be inserted in a sewing technique whereby the fiber is fed from a continuous spool through a needle-pointed mandrel guide which pierces a thin, disposable retention material at the top and bottom of the fastener to suspend the fiber in a relatively taut condition until the sealing at the ends of the casing 624 is completed. The polyurethane or silicone sealing material is then inserted into the respective ends of the casing 624, e.g., through the recesses 628, and curing then completed. Depending on the viscosity of the sealing medium used to form the plugs 630 and 632, centrifuging may be employed to force the sealing material toward the ends of the casing 624.

In the drawing, the interface 610 is also seen to include a sealing flange 634, for purposes hereinafter described. The flange 634 may be a threaded member to facilitate the fastening of the interface 610 into other apparatus. In addition, twist-lock fasteners, tapered slip-fit points or other retaining means and gaskets to facilitate the retention and release of the interface 610 in other apparatus, and the sealing of the upper growing portion 614 from the nutrient flow, may be employed as later described.

One use of the interface 610 may be shown in combination with the growth chamber 510, which is shown in FIGS. 11. The receptacles 540 of the growth chamber 510 can readily be adapted to securely retain the fastener 610, by appropriate retention or fastener means therebetween. The dimensions of the fastener 610 may be altered, or engaging means such as turning lugs included, so that the interface 610 can be inserted, fastened and the flanges 634 can be adapted to provide sealing means between the growth surface 620 of the interface and the nutrient solution chamber 514 of the growth chamber. The interface 610 is disposed in a manner so that the hollow fibers 626, within the casing 624, are in contact with the nutrient solution so that nutrients are wicked to the sponge 516, through the perforate surface 620 and to the growing plants. The sealing of the growth surface from the nutrient solution is of significant importance in the growth of shoots, due to the fact that the influx of pathogens to the plants is blocked by the minimal porosity of the hollow fibers. Accordingly, external contaminants cannot reach the growing plants, and any internal contaminants (produced within the plant itself) cannot pass from the individual interface unit 610 and cross-contaminate the medium which is shared with other growing shoots. It has been shown, for example, that fungus which has infiltrated a nutrient solution reservoir will cover the solution therein, including the surface of the casing 624, but that none of this fungus follows the nutrient solution through the fibers into the sponge 618.

With respect to the use of the growth chamber 510, it has been found that an adjustable vapor diffusion means 536 may be constructed whereby the adaptation and hardening of a growing plant to natural humidity are greatly facilitated. A series of holes or perforations of increasing diameter or surface area can be formed or otherwise provided in the cover 524, each of which is sealed with a diffusion membrane means. The diffusion membrane may be the same for each of the holes. A sliding cover enables the covering of all holes, or the exposure of one or more, depending on the humidity required within the growth chamber. It has been found that the permeability of the diffusion membranes is significantly dependent on the surface area of the membrane, and thus the progressive uncovering of larger holes allows more diffusion of vapor.

When used in connection with the chamber 510, when the shoot and root formation is of sufficient size and is physiologically prepared for existence in a natural environment, the shoot need not be removed from the surface 620, but the entire combination of the plant and the interface 610 may be easily removed and planted to minimize temporary damage to the plant. In addition, it will be apparent that the interface 610 could be employed as the initial interface for the growth of explant tissue, and once the shoot has grown to an appropriate size the shoots and the interface can be transferred to a growth chamber as a unit. Thus, shoots can be formed, grown to significant size, and transferred to environments for further grow-out without having to separate the plant xylem from the artificial xylem interface.

An alternative use is shown by the use of the cap 636 in FIG. 12. This cap may be constructed from a variety of resilient or other resinous material, and is seen to include an upper sealing surface 638 and a basin 640 formed by a side wall 642. Following the initial growth of the plant in a growth chamber, the basin 640 may be partially filled with growth medium and the casing 624 is then inserted into the cap 636, as shown by the arrow on FIG. 12. The solution is then sealed around the wicking fibers by the sealing means 634 and 638, allowing transport of the rootless plant to the next growth cycle, or shipment to final use, without disruption of nutrient feed to the living portion.

Turning to FIG. 13, additional apparatus which is used to accomplish this objective is shown.

In that Figure, a rooting cartridge 650 is seen to comprise an essentially bell-shaped core of open-cell sponge material 652. While a wide variety of pre-formed or molded cellular sponges may be employed, use of a polyvinyl acetyl sponge such as the Merocel sponge has again been found to be advantageous. The sponge 652 is seen to be covered by a non-toxic, essentially non-permeable covering 654. This covering has been formed from a food-grade vinyl coating known as "plastisol", and preferably is a non-leaching plastisol. Alternatively, a non-leaching coating can be applied to the sponge prior to the vinyl coating to function as a barrier against the perfusion of the coating into the sponge and to facilitate removal of the coating at time of planting in soil. A wide variety of methods and compositions may be employed for the coating of the sponge 52, if the coating is non-permeable so as not to inhibit plant growth. Preferably, the liquid-applied vinyl (i.e., plastisol) is applied by dipping the sponge in the liquid, followed by curing of the coating.

In the embodiment shown in FIG. 13, the rooting cartridge 650 is seen to include a xylem interface 656 mounted atop a cylindrical collar 658. The interface 656 may be any perforate surface which will mate with the xylem tissue of the plant, although in this instance the use of the track-etch, capillary-pore membrane manufactured by Nuclepore Corporation having a thickness of 2 to 4 mils, and perforations of about 0.2 microns on 10-30 micron centers is advantageous. However, as mentioned above, any factitious surface having perforations which will mate with some or all of the natural plant xylem tissue is within the purview of this invention. The membrane 656 and collar 658 may be assembled previously, such as by securing the flexible Nuclepore membrane to the collar with appropriate adhesive, and inserted into a cylindrical opening 660 in the body of the rooting cartridge 650. Preferably, this insertion is performed prior to the coating of the sponge 652 with plastisol, and the perforate surface of the membrane 656 is protected by a protective covering, not specifically shown, which is retained by lugs 662 on the interior surface of the cylindrical collar 658. In this regard, the collar 658 is made of a resilient resinous material, i.e., the collar and the lugs 662 have sufficient memory to permit expansion to permit the insertion and removal of appropriate objects, and the sealing of the inserted object against the transfer of liquid to the xylem interface 656, as hereinafter described.

This insertion and sealing will be described in more detail with respect to a wicking cartridge 664 which is seen to be disposed within the cylindrical opening 660. This cartridge is seen to include a casing 666 which comprises a lower sheath-like portion 668 and an upper basin portion 670. The portions 668 and 670 may be identical to the portions 612 and 614 in FIG. 12, aside from the fact that the xylem interface 656 in FIG. 13 is shown to be separate from the basin portion 670. The lower portion 668 includes, although not specifically shown, hollow fibers embedded in a sealing resin at either end of the portion 668, with the ends of the fibers extending into a sponge 672 which extends above the basin portion 670. The lower portion 668 also includes recesses 674 which permit liquid to contact the hollow fibers within the sheath portion 668 when that portion is immersed in liquid. As described in more detail in FIG. 12, which describes a fiber, sheath and sponge arrangement which is identical to that of the cartridge 664, liquid flows by capillary action through the porous walls of the fibers, through the lumens, to the sponge 672.

After formation of the sponge 652, insertion of the xylem interface 656 and collar 658, and coating of the assembly, the wicking cartridge 664 is inserted into the cylindrical opening 660 and elevated until the circumferential tang 675 on the basin portion 670 is inserted between the lugs 662 of the collar 658. When so disposed, the sponge 672 abuts the xylem interface 656 so that any nutrient medium wicked to the sponge is transferred through the perforate surface to be absorbed by the natural plant xylem tissue, and the abutting of the tang 675 with the collar 658 seals the wicking cartridge 664 within the rooting cartridge 650.

The construction of the rooting cartridge 650 facilitates the insertion of the shoot or explant tissue which is to be grown on the xylem surface 656. The circular tang 673 is seen to include the resilient collar 658 and the lugs 662 in a manner which minimizes or eliminates the flow of pathogens therebetween.

The construction of the rooting cartridge 650 facilitates the insertion of the shoot or explant tissue onto the artificial xylem surface 656. Specifically, the vinyl coating 654 is seen to cover a channel 676 which communicates with the perforate xylem surface. When a shoot or explant material is to be inserted, the vinyl is pierced directly above the channel, and the vinyl above the channel 676, and the channel itself, is expanded with a mandrel to permit the insertion of the material onto the xylem surface. A number of manufacturing techniques may be employed in this regard. For example, prior to the insertion of the wicking cartridge 664, the shoot may be inserted with a mandrel into the channel 676 and a vacuum applied through the cylindrical opening 660 to pull the shoot tightly against the xylem surface. Immediately thereafter, the cartridge 664 is inserted to permit the profusion of the nutrient medium to the plant. Channel 676 and the size of the opening formed in the vinyl covering may be appropriately sized to retain the shoot firmly against the perforate surface during this procedure. It should be noted that both the vinyl covering and the sponge 652 offer sufficient resilience to permit significant expansion of the shoot during growth.

Cell culture can be injected through the vinyl covering onto the perforate surface with a hypodermic needle. In this regard, a tubular member may be cast within the channel 676 and extend above the top of the rooting cartridge 650. Cell culture can be injected through the top of this tubular member onto the perforate surface, and the top may be clipped off after the shoot has formed to permit further growth. Thus, the sterility of the growing tissue is not compromised until the shoot has formed and natural plant callus has covered the surface 656 and sealed the vascular system against the influx of pathogens.

Depending upon the type of growth required and the particular varietal grown, the rooting cartridge 650 may be equipped with one or more aeration port 680 which provides a proper air-medium mixture to the sponge 652. Multiple aeration ports may be provided depending upon the sponge size and density, and the particular varietal being grown therein. The port 680 is formed by coating a protrusion on the sponge with the plastisol and, after coating, shearing the end of the protrusion with a knife to expose the sponge. Thereafter, a cap 682 which includes a hydrophilic membrane 684 is bonded to the port 680 to provide the proper gas exchange with the sponge for proper air-medium ratio. The hydrophilic membrane 684 is similar to the membrane 436 described with respect to FIG. 9.

The lower portion of FIG. 13 shows a medium delivery and support device 710 which provides mechanical support to the rooting cartridge 650. The device 710 is molded of high-impact resistant, autoclavable polymeric material such as polycarbonate. The device is a sterile reservoir designed to accept plant growth liquid medium for the rooting cartridge 650. In this embodiment, the device comprises a rigid polymeric casing 712 which forms a cylindrical side wall 714, a central retaining stanchion 716 and an inner protrusion 718. The stanchion 716 includes a removable insert 720 comprising a cylindrical, threaded collar 722 bearing a first and second silicone diaphragm 724 and 726, respectively. Each of these diaphragms is perforated at the center to form a passageway 728.

The side wall 714 is seen to include a fluid inlet 730 and a fluid outlet 732. Fluid enters a reservoir 734 which is formed by the walls of the device 710, and fills the interior reservoir 734 until the liquid rises to the level of the lower diaphragm 726. The outlet port 732 is positioned at a height which controls this liquid level.

After the shoot or plant tissue has been appropriately placed, on the perforate surface 656 in the rooting cartridge 650, and the wicking cartridge 664 inserted as described, the entire rooting cartridge 650 is then placed in the device 710. As the rooting cartridge 650 is lowered into the device 710, the sponge 652 is wedged tightly between the side wall 714 and the stanchion 716, and the sheath portion 668 enters the passageway 728. Upon complete insertion, the diaphragms 724 and 726 enter a retaining groove 686 on the wicking cartridge 664, to close the reservoir 734 to the outside environment. In addition, the basin portion 670 of the wicking cartridge 664 is seen to engage tightly with the collar 722 to provide additional sealing to the transmission of pathogens to the nutrient medium.

The use of the rooting cartridge 650 will be apparent in the context of the previous description of the induction of lateral root formation into the sponge 570 in FIG. 11A. In this instance, however, the rooting cartridge 650 may be planted in toto after removal or partial removal of the coating 654 and hardening of the roots within the sponge 652. The overall shape of the cartridge 650, and the device 710, facilitates the development of a root ball and the rooting cartridge 650 may be easily transferred to soil or soil-like medium for ultimate plant growth. As an alternative to the removal or partial removal of the coating 654, this coating may be partially degradable over time to allow the eventual growth of the roots into the soil when planted.

From the foregoing description, one skilled in the art can readily ascertain the essential characteristics of the invention and, without departing from the spirit and scope thereof, can adapt the invention to various usages and conditions. Changes in form and the substitution of equivalents are contemplated as circumstances may suggest or render expedient; and although specific terms have been employed herein, they are intended in a descriptive sense and not for purposes of limitation, the purview of the invention being delineated in the following claims.

TABLE 1

| Item No. | Component | Amount per liter of culture solution (final concentration in culture solution) |
|---|---|---|
| | Macroelements | |
| 1 | Ammonium nitrate $NH_4NO_3$ | 165 mg |
| 2 | Potassium nitrate, $KNO_3$ | 190 mg |
| 3 | Calcium chloride $CaCl_2.2h_2O$ | 44 mg |
| 4 | Magnesium sulfate, $MgSO_4.7H_2O$ | 37 mg |
| 5 | Potassium phosphate, $KH_2PO_4$ | 17 mg |

TABLE 1-continued

| Item No. | Component | Amount per liter of culture solution (final concentration in culture solution) |
|---|---|---|
| 6 | Chelated iron | |
| | a) Na2EDTA | 37.3 mg |
| | b) Ferrous sulfate, $FeSO_4.7H_2O$ | 27.8 mg |
| 7 | Microelements | |
| | a) Boric acid, $H_3BO_3$ | 6.2 mg |
| | b) Manganese sulfate, $MnSO_4.4H_2O$ | 22.3 mg |
| | c) Zinc sulfate, $ZnSO_4.7H_2O$ | 8.6 mg |
| | d) Potassium iodide, KI | 0.83 mg |
| | e) Sodium molybdate, $Na_2MoO_4.2H_2O$ | 0.25 mg |
| | f) Copper sulfate, $CuSO_4.5H_2O$ | 0.025 mg |
| | g) Cobalt chloride, $COCl_2.6H_2O$ | 0.025 mg |
| 8 | myo Inositol | 100 mg |
| 9 | Naphthaleneacetic acid (NAA) | 0.1 mg |
| 10 | Thiamine HCl (vitamin $B_1$) | 0.4 mg |
| 11 | Polyvinyl-polypyrrolidone | 1.80 g |
| 12 | Sucrose | 30 g |
| 13 | Water, distilled | to 1000 ml |

I claim:

1. An apparatus for supporting the growth of a vascular plant which includes natural xylem tissue, the apparatus comprising an artificial surface including lumens having a size of up to about 120 microns, the artificial surface capable of being placed in contact with an transferring liquid only through the lumens to the natural xylem tissue.

2. The apparatus of claim 1 which also includes means for providing a nutrient solution to the lumens, and wherein the means for providing a nutrient solution to the lumens includes means for maintaining the nutrient solution under sterile conditions.

3. A growth apparatus for providing nutrient solution to the natural xylem tissue of a living shoot, comprising an artificial surface including lumens having a size of up to about 120 microns, the artificial surface being capable of transferring the nutrient solution only through the lumens to the natural xylem tissue; and capillary transport means in contact with the perforate surface adapted to cause the transfer of nutrient solution to the artificial surface while serving as a barrier to the transport of pathogens to the natural xylem tissue with the nutrient solution.

4. The growth apparatus of claim 3 wherein the capillary transport means comprises at least one hollow fiber which transports nutrient solution through a lumen from a reservoir to the perforate surface, the fiber having a wall porosity of from about 0.01 to about 0.45 microns.

5. The growth apparatus of claim 4 wherein the artificial surface is disposed within a cavity which is adapted to be maintained in a sterile condition during plant growth.

6. A growth apparatus for a vascular plant having xylem tissue, comprising:
a body portion supporting an artificial xylem surface characterized by having a plurality of lumens having a diameter of up to about 120 microns adapted to transfer liquid only through the lumens to the natural xylem tissue of the vascular plant;
capillary transport means being supported in the container such that a first end of the capillary transport means extends into a chamber adapted to contain a nutrient medium and a second end is disposed in fluid communication with the artificial xylem surface; and
a top cover attached to and sealed against the body portion and adapted to form a sterile cavity over the artificial xylem surface.

7. A method for growing a plant having natural xylem tissue, comprising:
providing an element having an artificial surface, the surface having lumens of a size of up to about 120 microns;
placing the natural xylem tissue of the plant on the artificial surface; and
applying a liquid to the artificial surface to cause the liquid to flow only through the lumens to the natural xylem tissue, and in a manner which encourages the growth of the plant tissue to form aerial portions of the plant.

8. An apparatus for supporting the growth of a vascular plant which includes natural xylem tissue, the apparatus comprising an artificial surface including perforations having a size of up to about 120 microns, the artificial surface capable of being placed in contact within and transferring liquid to the natural xylem tissue, and porous hydrophobic means for providing oxygen to the liquid.

* * * * *